(12) United States Patent
Fukuda et al.

(10) Patent No.: US 10,732,168 B2
(45) Date of Patent: Aug. 4, 2020

(54) CELL IMAGING DEVICE, CELL IMAGING METHOD, AND SAMPLE CELL

(71) Applicant: Sysmex Corporation, Kobe-shi, Hyogo (JP)

(72) Inventors: Masakazu Fukuda, Kobe (JP); Masamichi Tanaka, Kobe (JP); Yanyan Liu, Kobe (JP); Ryosuke Fujii, Kobe (JP); Takumi Inutsuka, Kobe (JP); Tomoyuki Tsukahara, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 0 days.

(21) Appl. No.: 15/628,188

(22) Filed: Jun. 20, 2017

(65) Prior Publication Data

US 2017/0285000 A1  Oct. 5, 2017

Related U.S. Application Data

(63) Continuation of application No. PCT/JP2015/006469, filed on Dec. 25, 2015.

(30) Foreign Application Priority Data

Dec. 26, 2014 (JP) ................................ 2014-265931
Dec. 26, 2014 (JP) ................................ 2014-265984

(51) Int. Cl.
*G01N 21/00* (2006.01)
*G01N 33/50* (2006.01)
(Continued)

(52) U.S. Cl.
CPC ............... *G01N 33/50* (2013.01); *C12Q 1/68* (2013.01); *G01N 15/00* (2013.01); *G01N 15/14* (2013.01);
(Continued)

(58) Field of Classification Search
CPC .......... G01N 21/6428; G01N 21/6486; G01N 21/6458; G01N 21/645; G01N 15/1459
See application file for complete search history.

(56) References Cited

U.S. PATENT DOCUMENTS 5,159,403 A   10/1992  Kosaka
6,493,135 B1  12/2002  Engelhardt
(Continued)

FOREIGN PATENT DOCUMENTS

CN   102414562 A   4/2012
CN   103648649 A   3/2014
(Continued)

OTHER PUBLICATIONS

Extended European Search Report for European Application No. 15872299.1, dated Jul. 19, 2018, pp. 1-10.
(Continued)

*Primary Examiner* — David P Porta
*Assistant Examiner* — Mamadou Faye
(74) *Attorney, Agent, or Firm* — Brinks Gilson & Lione

(57) ABSTRACT

Provided are a cell imaging device and a cell imaging method that can shorten the time period of taking images of cells in a liquid sample, compared with conventional techniques. This cell imaging device introduces a urine sample containing cells into an internal space of a sample cell, moves at least one of the sample cell and an objective lens in a second direction while at least one of the sample cell and the objective lens is moved in a first direction, the second direction being different from the first direction, and takes, at a plurality of imaging positions, images of cells contained in the urine sample by means of an imaging unit.

19 Claims, 17 Drawing Sheets

(51) Int. Cl.
*G01N 33/483* (2006.01)
*G02B 21/36* (2006.01)
*G01N 21/17* (2006.01)
*G01N 15/00* (2006.01)
*G01N 15/14* (2006.01)
*G01N 21/01* (2006.01)
*G02B 21/26* (2006.01)
*G01N 33/493* (2006.01)
*G02B 21/30* (2006.01)
*C12Q 1/68* (2018.01)
*A61B 5/00* (2006.01)
*A61B 10/00* (2006.01)
*G01B 11/00* (2006.01)

(52) U.S. Cl.
CPC ......... *G01N 15/1468* (2013.01); *G01N 21/01* (2013.01); *G01N 21/17* (2013.01); *G01N 33/483* (2013.01); *G01N 33/493* (2013.01); *G02B 21/26* (2013.01); *G02B 21/30* (2013.01); *G02B 21/36* (2013.01); *G02B 21/367* (2013.01); *A61B 5/00* (2013.01); *A61B 10/00* (2013.01); *G01B 11/00* (2013.01); *G01N 2015/1452* (2013.01)

(56) References Cited

U.S. PATENT DOCUMENTS

| | | | |
|---|---|---|---|
| 9,671,407 B2 * | 6/2017 | Mikolajczyk | G01N 33/54306 |
| 2004/0239916 A1 * | 12/2004 | Seino | G01N 15/1475 356/28.5 |
| 2004/0256538 A1 | 12/2004 | Olson et al. | |
| 2007/0009395 A1 * | 1/2007 | Jiang | B01L 9/523 422/82.08 |
| 2007/0035819 A1 * | 2/2007 | Bahatt | G01N 21/0332 359/366 |
| 2008/0160634 A1 * | 7/2008 | Su | G01N 27/74 436/501 |
| 2009/0002811 A1 * | 1/2009 | Uchiyama | G02B 21/241 359/383 |
| 2009/0103588 A1 | 4/2009 | Umemura | |
| 2009/0206234 A1 * | 8/2009 | Okuda | G01J 3/46 250/201.2 |
| 2009/0231689 A1 * | 9/2009 | Pittsyn | G01B 9/04 359/363 |
| 2011/0085031 A1 * | 4/2011 | Park | G02B 21/0008 348/79 |
| 2011/0134516 A1 | 6/2011 | Araya et al. | |
| 2012/0076349 A1 | 3/2012 | Manri et al. | |
| 2012/0293796 A1 * | 11/2012 | Ludowise | B01L 3/5027 356/244 |
| 2014/0193892 A1 | 7/2014 | Mohan et al. | |
| 2015/0309299 A1 | 10/2015 | Watanabe | |
| 2017/0059566 A1 * | 3/2017 | Reed | G01N 33/56911 |

FOREIGN PATENT DOCUMENTS

| | | |
|---|---|---|
| EP | 1865354 A1 | 12/2007 |
| JP | H04-188042 A | 7/1992 |
| JP | H11-095091 A | 4/1999 |
| JP | 2001-255260 A | 9/2001 |
| JP | 2005527827 A | 9/2005 |
| JP | 2007-171582 A | 7/2007 |
| JP | 2007-248501 A | 9/2007 |
| JP | 2011-141286 A | 7/2011 |
| JP | 2011-209573 A | 10/2011 |
| JP | 2014-134632 A | 7/2014 |
| WO | WO 2008/007725 A1 | 1/2008 |
| WO | WO 2010/140460 A1 | 12/2010 |
| WO | WO 2014/109095 A1 | 7/2014 |

OTHER PUBLICATIONS

Office Action in Japanese Application No. 2017-247505, dated Jan. 8, 2019, 2 pages.
The first Chinese Office Action dated Feb. 3, 2019 in a counterpart Chinese patent application No. 201580069054.6.
The second Chinese Office Action dated Sep. 27, 2019 in a counterpart Chinese patent application No. 201580069054.6.
The third Chinese Office Action dated Mar. 16, 2020 in a counterpart Chinese patent application No. 201580069054.6.

* cited by examiner

CELL IMAGING DEVICE, CELL IMAGING METHOD, AND SAMPLE CELL

RELATED APPLICATIONS

This application is a Continuation of International Application No. PCT/JP2015/006469, filed on Dec. 25, 2015, which in turn claims the benefit of Japanese Patent Applications No. 2014-265931 and No. 2014-265984 filed on Dec. 26, 2014, the disclosures of which Applications are incorporated by reference herein.

BACKGROUND OF THE INVENTION

1. Field of the Invention

The present invention relates to a cell imaging device, a cell imaging method, and a sample cell for taking an image of a cell contained in a liquid sample.

2. Description of the Related Art

International Publication WO2008/007725 discloses an analyzer which takes images of particles included in urine in a preparation placed on a stage, and which analyzes the particles by using the obtained images. International Publication WO2008/007725 also indicates that: in order to avoid occurrence of focal displacement due to manufacturing errors of each preparation, a focusing mark is provided on one face of a glass slide of a coverslip; and focusing adjustment is performed such that the focal point is at the focusing mark. In International Publication WO2008/007725, the analyzer moves the stage by a predetermined distance in the vertical direction relative to the objective lens from the focusing position obtained through focusing adjustment using the focusing mark, and sets an analysis start position at which observation of particles is to be started. Next, the stage is moved in the vertical direction by a very small distance from the analysis start position. Then, when a focused state is detected, it is determined that a particle is present at the focusing position, and an image of the particle is taken at the focusing position. Subsequently, in order to take an image of a new particle in a different visual field region, the stage is moved in the horizontal direction and then stopped, the stage is moved up and down by a predetermined distance in the vertical direction relative to the focusing position of the immediately-preceding visual field region. Then, when a focused state is detected, an image of the particle is taken at this focusing position.

In the analyzer disclosed in International Publication WO2008/007725, the relative distance between the stage and the objective lens is changed in the vertical direction in each visual field region to detect a focusing position, and taking an image of a particle is performed at the detected focusing position. Thus, it takes a long time to take an image. In addition, every time the stage is moved to a new visual field region, the stage is moved in the horizontal direction and then stopped, and thus, particles in the preparation vibrate due to the stop of the stage. Therefore, in order to obtain a clear image of a particle, it is necessary to wait until such particle vibration stops. Thus, it could take a long time to take an image.

SUMMARY OF THE INVENTION

A cell imaging device includes: sample cell including an internal space for holding a liquid sample containing cells; an imaging unit including an objective lens and configured to take images of cells contained in the liquid sample held in the internal space; a first drive unit configured to move at least one of the sample cell and the objective lens in a first direction; a second drive unit configured to move at least one of the sample cell and the objective lens in a second direction that is different from the first direction; and a controller configured to control the first drive unit, the second drive unit, and the imaging unit such that images of cells contained in the liquid sample held in the internal space are taken at a plurality of imaging positions, while at least one of the sample cell and the objective lens is moved in the second direction while at least one of the sample cell and the objective lens is moved in the first direction.

A cell imaging method includes: introducing a liquid sample containing cells into an internal space of a sample cell; and taking, at a plurality of imaging positions, images of cells contained in the liquid sample held in the internal space, while moving at least one of the sample cell and the objective lens in a second direction while moving at least one of the sample cell and the objective lens in a first direction, the second direction being different from the first direction.

A cell imaging device includes: a sample cell comprising an internal space for holding a liquid sample containing cells, and a first reference mark and a second reference mark which are distanced from each other; an imaging unit comprising an objective lens and configured to take images of cells contained in the liquid sample held in the internal space; a first drive unit configured to move at least one of the sample cell and the objective lens in a first direction; a second drive unit configured to move at least one of the sample cell and the objective lens in a second direction that is different from the first direction; and a controller configured to, on the basis of a first focusing position of the objective lens with respect to the first reference mark and a second focusing position of the objective lens with respect to the second reference mark, control the second drive unit so as to move in the second direction at least one of the sample cell and the objective lens, and control the first drive unit so as to move in the first direction at least one of the sample cell and the objective lens, the controller configured to control the imaging unit so as to take, at a plurality of imaging positions, images of cells contained in the liquid sample held in the internal space.

A cell imaging method includes: detecting a first focusing position of an objective lens with respect to a first reference mark of a sample cell and a second focusing position of the objective lens with respect to a second reference mark of the sample cell; introducing a liquid sample containing cells, into an internal space of the sample cell; and on the basis of the detected first focusing position and the detected second focusing position, moving at least one of the sample cell and the objective lens in a second direction, and moving at least one of the sample cell and the objective lens in a first direction that is different from the second direction, and taking, at a plurality of imaging position, images of cells contained in the liquid sample held in the internal space.

A sample cell having an internal space for holding a liquid sample containing cells includes: a flow-in part for introducing the liquid sample into the internal space; a flow-out part for discharging the liquid sample from the internal space; a first reference mark provided at a position to the flow-in part side in the internal space, and configured to be used in focal point adjustment for taking images of the cells; and a second reference mark provided at a position to the flow-out part side in the internal space, and configured to be used in focal point adjustment for taking images of the cells.

According to the present invention, the time period of taking images of cells in a liquid sample can be shortened compared to conventional techniques.

These and other objects, features, aspects, and effects of the present invention will become more apparent from the following detailed description when taken in conjunction with the accompanying drawings.

DETAILED DESCRIPTION OF THE PREFERRED EMBODIMENTS

Hereinafter, preferred embodiments are described with reference to the drawings.
(Embodiment 1)
<Configuration of Cell Imaging Device>

Figure 1:
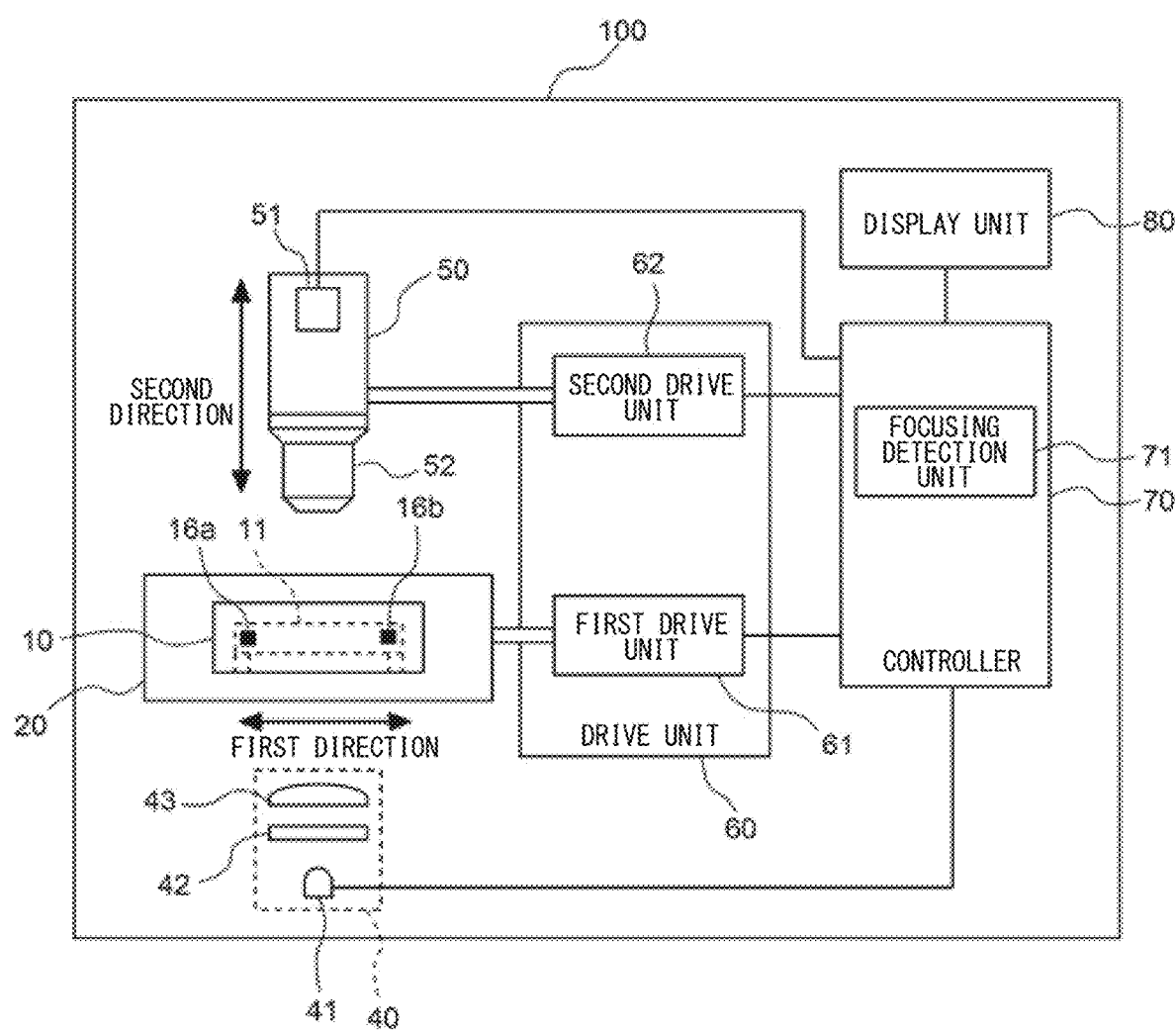
FIG. 1 is a schematic diagram showing a configuration of a cell imaging device according to Embodiment 1.

With reference to FIG. 1, a configuration of a cell imaging device is described. A cell imaging device 100 includes a sample cell 10, a placement unit 20, a light source unit 40, an imaging unit 50, a drive unit 60, a controller 70, and a display unit 80. The cell imaging device 100 is a device that takes images of cells contained in a liquid sample such as, for example, cells in a urine sample collected from a subject. The cell imaging device 100 is configured to fill a urine sample into the sample cell 10 and to take images of cells in the sample cell 10 by means of the imaging unit 50 while the sample cell 10 is moved in the horizontal direction. The liquid sample as the imaging target may be any biogenic sample that contains a plurality of kinds of cells having different sizes, and may be blood, celomic fluid, or uterine cervix tissue, for example.

Figure 2:
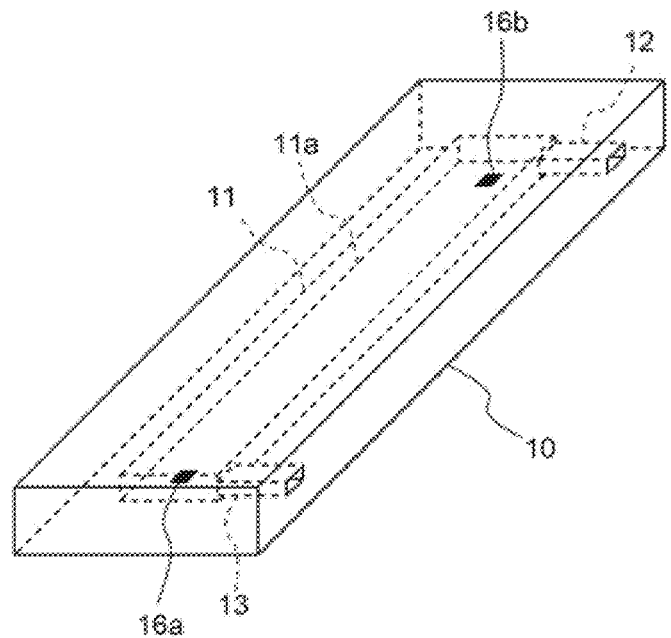
FIG. 2 is a perspective view showing a configuration of a sample cell according to Embodiment 1.

FIG. 2 is referred to. The sample cell 10 includes: an internal space 11 for holding a urine sample; an inlet 12 connected to the internal space 11; and an outlet 13 connected to the internal space 11. The sample cell 10 has a flat rectangular parallelepiped shape elongated in one direction, and is formed from a translucent material. The internal space 11 is a space having a flat rectangular parallelepiped shape elongated in one direction, and is provided inside the sample cell 10. The longitudinal direction of the internal space 11 is the same as the longitudinal direction of the sample cell 10. Each face of the internal space 11 is flat.

From one end of the internal space 11, the inlet 12 extends in a direction perpendicular to the longitudinal direction. From the other end of the internal space 11, the outlet 13 extends in the same direction as the inlet 12. Each of the inlet 12 and the outlet 13 is open at one lateral face of the sample cell 10.

The sample cell 10 includes: a first reference mark 16a at a position to the outlet 13 side of the internal space 11; and a second reference mark 16b at a position to the inlet 12 side of the internal space 11. The first reference mark 16a and the second reference mark 16b are each provided on a bottom face 11a of the internal space 11.

The first reference mark 16a and the second reference mark 16b may be provided at a place other than the bottom face 11a of the internal space 11, such as the top face or the bottom face of the sample cell 10, the top face of the internal space 11, or the like.

Figure 3:
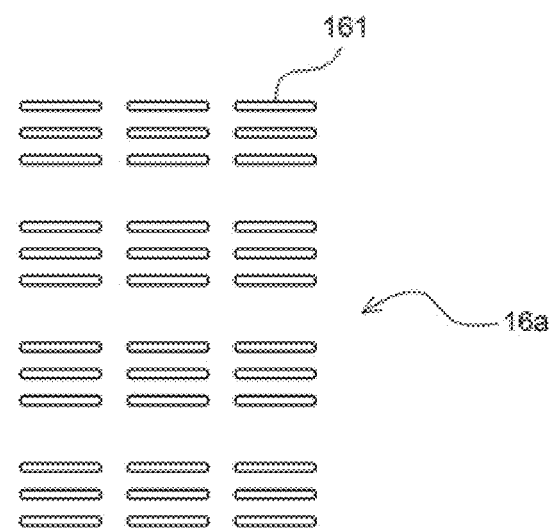
FIG. 3 is a diagram showing a configuration of a reference mark.

With reference to FIG. 3, the shape of the first reference mark 16a is described. Since the shape of the second reference mark 16b is the same as the shape of the first reference mark 16a, description of the shape of the second reference mark 16b is omitted. The first reference mark 16a includes a plurality of minute grooves 161 each formed through laser beam machining. The line width of each minute groove 161 is several micrometers and the length thereof is several tens micrometers. Three minute grooves 161 that are parallel to one another are regarded as one set, and a plurality of sets of the minute grooves 161 are formed in a rectangular region, whereby the first reference mark 16a is formed. The longitudinal direction of each minute groove 161 extends in the same direction as the longitudinal direction of the internal space 1 of the sample cell 10.

Figure 4:
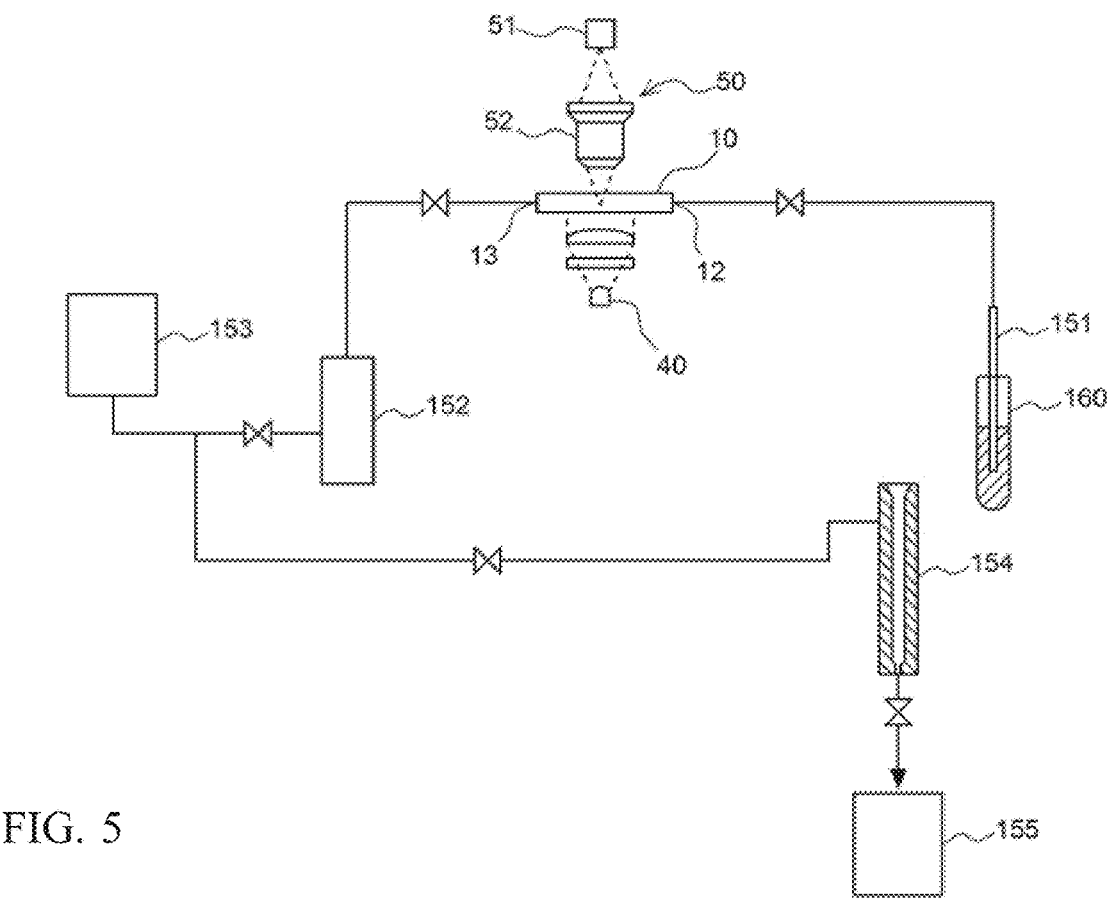
FIG. 4 is a schematic diagram showing a fluid circuit of the cell imaging device.

FIG. 4 is referred to. The inlet 12 of the sample cell 10 is connected to an aspiration tube 151 via a tube and a solenoid valve. The outlet 13 of the sample cell 10 is connected to a pump 152 via a tube and a solenoid valve. The pump 152 is connected via a tube and a solenoid valve to a container 153 that contains a buffer solution. The buffer solution is filled in the tube for urine sample introduction. The container 153 is connected to a washing vessel 154 via a tube and a solenoid valve. Buffer solution is supplied to the washing vessel 154 and is also used as a washing liquid. A waste liquid container 155 is provided below the washing vessel 154.

The aspiration tube 151 is inserted in a sample container 160 which is a urine collection tube. Through operation of the pump 152, the urine sample in the sample container 160 is aspirated from the aspiration tube 151. After a predetermined amount of the urine sample is aspirated, the aspiration tube 151 is pulled out of the sample container 160. The pump 152 continues operating also after the aspiration tube 151 has been pulled out of the sample container 160, whereby air is aspirated through the aspiration tube 151, and the urine sample is introduced from the inlet 12 into the internal space 11. By the pump 152 operating until the urine sample comes out of the outlet 13, the urine sample is filled in the entire internal space 11.

After images of cells contained in the urine sample are taken, washing of the aspiration tube 151 and the sample cell 10 is performed. For the washing, the aspiration tube 151 is moved to the washing vessel 154. Through operation of the pump 152, the buffer solution is supplied to the internal space 11, whereby the internal space 11 is washed. The urine sample pushed out of the internal space 11 is discharged through the aspiration tube 151 into the washing vessel 154. Through further operation of the pump 152, the buffer solution is discharged through the aspiration tube 151, whereby the inside of the aspiration tube 151 is washed. The washing vessel 154 is supplied with the buffer solution from the container 153, and the outside of the aspiration tube 151 is washed. The waste liquid from the washing vessel 154 is stored in the waste liquid container 155.

After the washing has been completed, the next urine sample is aspirated by the aspiration tube 151, to be introduced into the internal space 11 of the sample cell 10.

FIG. 2 is referred to, again. The sample cell 10 is fixed to the placement unit 20 such that the bottom face 11*a* provided with the first reference mark 16*a* and the second reference mark 16*b* are on the lower side in the internal space 11. The sample cell 10 is fixed to the placement unit 20 so as to be inclined by a predetermined angle in a predetermined direction relative to the horizontal direction. Even if the placement unit 20 is configured such that the sample cell 10 is not inclined relative to the horizontal direction, there are cases where the sample cell 10 becomes slightly inclined relative to the horizontal direction due to the difference among devices. The sample cell 10 becomes inclined upwardly relative to the horizontal direction in some cases, and downwardly relative to the horizontal direction in other cases. Therefore, in the present embodiment, the sample cell 10 is made inclined in advance in a predetermined direction relative to the horizontal direction, whereby, in the imaging operation described later, the direction in which an objective lens 52 is moved can be made constant for each urine sample, and the moving mechanism and the movement control for the objective lens 52 can be simplified.

The sample cell 10 is mounted to the placement unit 20 such that the sample cell 10 cannot be removed therefrom. The sample cell 10 may be made as a disposable sample cell. In this case, the placement unit 20 is configured such that the sample cell 10 is removable.

FIG. 1 is referred to, again. The drive unit 60 includes a first drive unit 61 and a second drive unit 62, and moves the sample cell 10 and the objective lens 52 of the imaging unit 50. The first drive unit 61 includes an electric motor. The placement unit 20 is moved by the first drive unit 61 in a first direction which is one direction in the horizontal direction. The first direction is a direction in which the internal space 11 is elongated.

Figure 5:
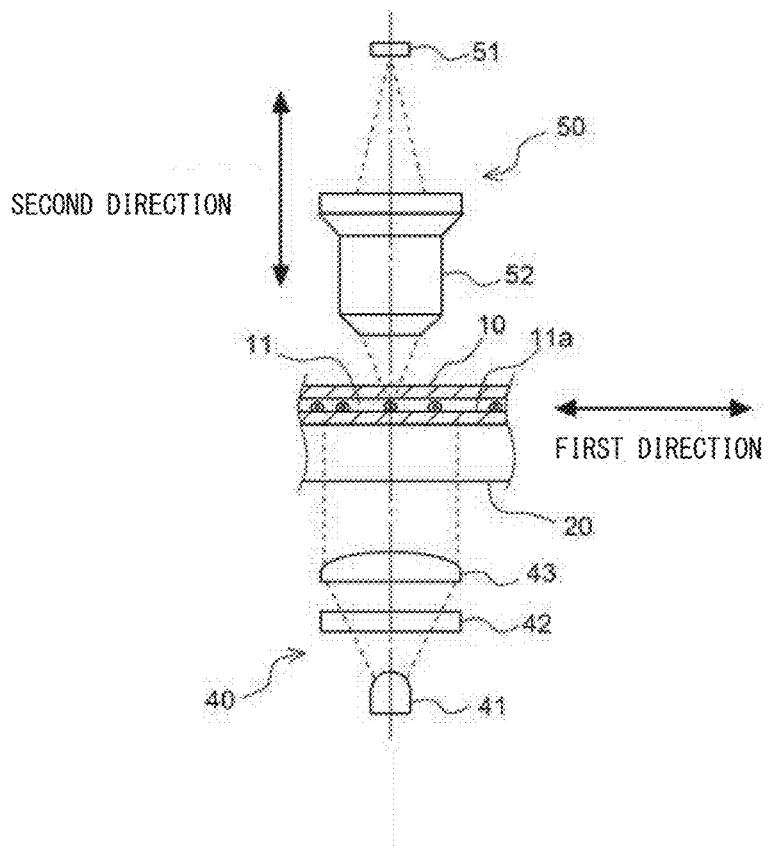
FIG. 5 is a front view showing configurations of a light source unit and an imaging unit.

FIG. 5 is referred to. The light source unit 40 is provided below the placement unit 20. The light source unit 40 includes an LED light source 41, a diffuser 42, and a lens 43. The light source 41 is a pulsed-light-emitting light source which emits pulsed light at equal intervals. Each lighting time period is 140 to 200 μsec. A second direction which is the optical axis direction of the light source unit 40 is a direction that crosses the horizontal direction. The second direction is the vertical direction, for example. In order to apply light to the sample cell 10, the light source 41 applies light upwardly. Above the light source 41, the diffuser 42 and the lens 43 are disposed. Light emitted from the light source 41 is diffused by the diffuser 42, and is made into collimated light by the lens 43. The collimated light is applied to the sample cell 10.

The imaging unit 50 is provided above the placement unit 20. The imaging unit 50 includes: an image pickup element 51 which is a CCD image sensor or a CMOS image sensor; and the objective lens 52. The image pickup element 51 and the objective lens 52 are disposed such that, along the same optical axis as that of the light source unit 40, the image pickup element 51 is at the upper side and the objective lens 52 is at the lower side. The image pickup element 51 and the objective lens 52 are held in one lens barrel. That is, the distance between the image pickup element 51 and the objective lens 52 is not changed. The magnification of the objective lens 52 is 15-fold, but is not limited to 15-fold as long as the magnification allows enlargement of, to an appropriate size, images of cells such as white blood cell, red blood cell, and epithelial cell, and other particles such as cast that are contained in urine.

FIG. 1 is referred to, again. The second drive unit 62 includes an electric motor. The imaging unit 50 is moved in the second direction by the second drive unit 62. By the imaging unit 50 being moved in the second direction, the focal point of the objective lens 52 is adjusted.

The controller 70 includes a microcomputer and a memory, and controls each of the light source unit 40, the imaging unit 50, the first drive unit 61, the second drive unit 62, and the display unit 80. The image obtained by the imaging unit 50 is provided to the controller 70. The controller 70 performs a predetermined process on the obtained image. The controller 70 includes a focusing detection unit 71 which performs automatic focusing operation for the imaging unit 50.

Image processing may be configured as a process that is performed by a personal computer. In this case, the controller 70 communicates with a personal computer, and transmits images of cells to the personal computer. The personal computer performs image processing such as cutting out a partial image for each cell.

The display unit 80 includes a liquid crystal display panel. The display unit 80 is connected to the controller 70, is controlled by the controller 70, and displays a screen. On the display unit 80, a taken image, a partial image obtained through image processing, or the like is displayed. When the image processing is performed by a personal computer, a taken image, or a partial image obtained through the image processing may be displayed on a display unit of the personal computer.

<Operation of Cell Imaging Device>

The cell imaging device 100 take images of, by means of the imaging unit 50, cells contained in a urine sample filled in the internal space 11 of the sample cell 10. In the imaging operation, while the sample cell 10 is moved at a constant speed in the first direction, the objective lens 52 is moved in the second direction at a uniform speed which is a moving speed according to the inclination of the sample cell 10, and images are taken in a plurality of visual fields of the imaging unit 50. Accordingly, without detecting the focused state in each visual field, it is possible to set the focal point to a vicinity of the bottom face of the internal space 11. The moving speed of the objective lens 52 in the second direction is determined during initialization operation of the cell imaging device 100 before taking images for the urine sample is performed. Such operation of the cell imaging device 100 is described below.

Figure 6:
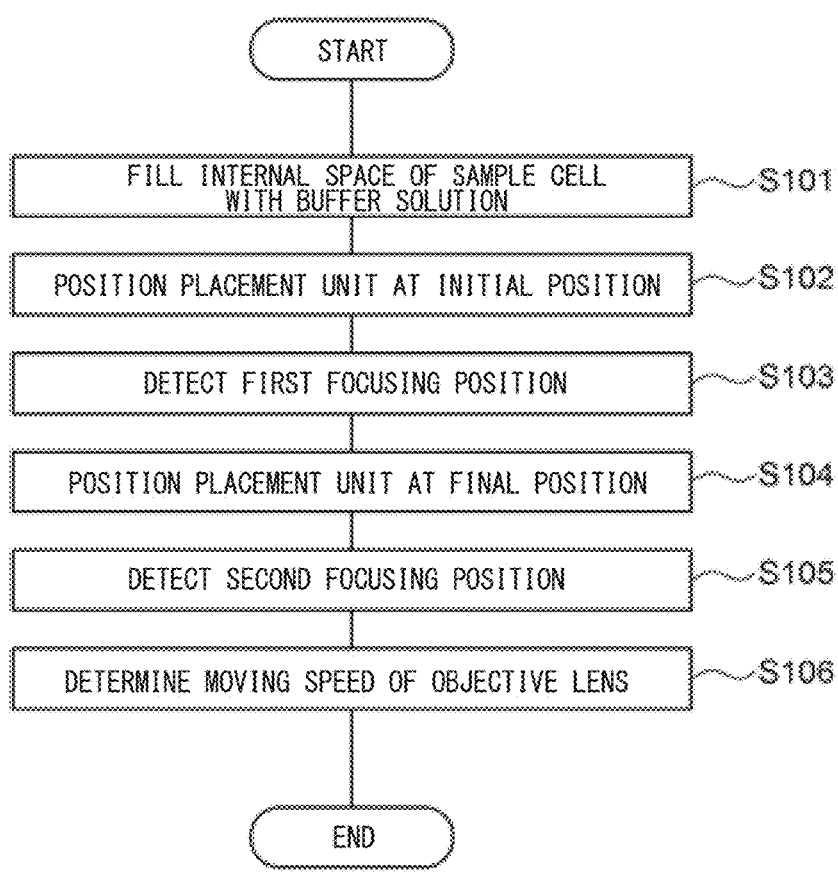
FIG. 6 is a flow chart showing the procedure of a moving speed determination operation according to Embodiment 1.

When a user activates the cell imaging device 100, the cell imaging device 100 performs an initialization operation. The initialization operation includes a moving speed determination operation for determining the moving speed of the imaging unit 50 used when images of cells in urine are taken. With reference to FIG. 6, the moving speed determination operation is described.

In step S101, the controller 70 controls the pump 152 to fill the flow path up to the aspiration tube 151 with the buffer solution from the container 153. As a result, the buffer solution is held in the internal space 11 of the sample cell 10.

In step S102, the controller 70 controls the first drive unit 61 to move the placement unit 20 such that the first reference mark 16a to the outlet 13 side of the sample cell 10 is disposed on the optical axis of the imaging unit 50. Hereinafter, the position of the placement unit 20 realized when the first reference mark 16a is disposed on the optical axis of the imaging unit 50 is referred to as "initial position". The position of the placement unit 20 realized when the second reference mark 16b to the inlet 12 side of the sample cell 10 is disposed on the optical axis of the imaging unit 50 is referred to as "final position".

In step S103, the controller 70 detects a first focusing position which is the focusing position of the objective lens 52 at the initial position. The controller 70 performs the automatic focusing operation three times in order to detect the first focusing position. In the automatic focusing operation, the second drive unit 62 moves the objective lens 52 in the second direction, and the focusing detection unit 71 detects a state where the focal point is at the first reference mark 16a.

The automatic focusing operation is of a contrast detection type. The position of the objective lens 52 at which the contrast of the image obtained by the image pickup element 51 is maximized is detected as the focusing position of the objective lens 52. The detected focusing position is stored in the memory of the controller 70.

An automatic focusing operation other than that of the contrast detection type may be employed. For example, a known automatic focusing operation of a type such as phase contrast detection type, line sensor type, ultrasound type, infrared radiation type, or the like may be employed.

Among the obtained three focusing positions, the controller 70 excludes one that has the most deviated numerical value indicative of the focusing position, and obtains the mean value of the remaining two focusing positions. The controller 70 stores in the memory the obtained mean value as the first focusing position.

In step S104, the controller 70 controls the first drive unit 61 to move the placement unit 20 to the final position.

In step S105, the controller 70 detects a second focusing position which is the focusing position of the objective lens 52 at the final position. In order to detect the second focusing position, the controller 70 performs the automatic focusing operation three times.

Among the obtained three focusing positions, the controller 70 excludes one that has the most deviated numerical value indicative of the focusing position, and obtains the mean value of the remaining two focusing positions. The controller 70 stores in the memory the obtained mean value as the second focusing position.

The number of times of execution of the automatic focusing operation in the detection of the first and second focusing positions is not limited to three, and may be one or a plural number other than three. However, increase in the number of times of the automatic focusing operation results in an increased operation time period, and thus, the number of times of the automatic focusing operation is preferably as small as possible. From the viewpoint of detection accuracy, it is preferable to perform the automatic focusing operation a plurality of times.

In the detection of the first focusing position, the mean value of two focusing positions is calculated. However, the first focusing position is not limited thereto. The first focusing position may be the mean value of three focusing positions, or may be the middle one among the three focusing positions. The same applies to the second focusing position.

In step S106, the controller 70 determines the moving speed of the objective lens 52 by using the first focusing position and the second focusing position.

Figure 7:
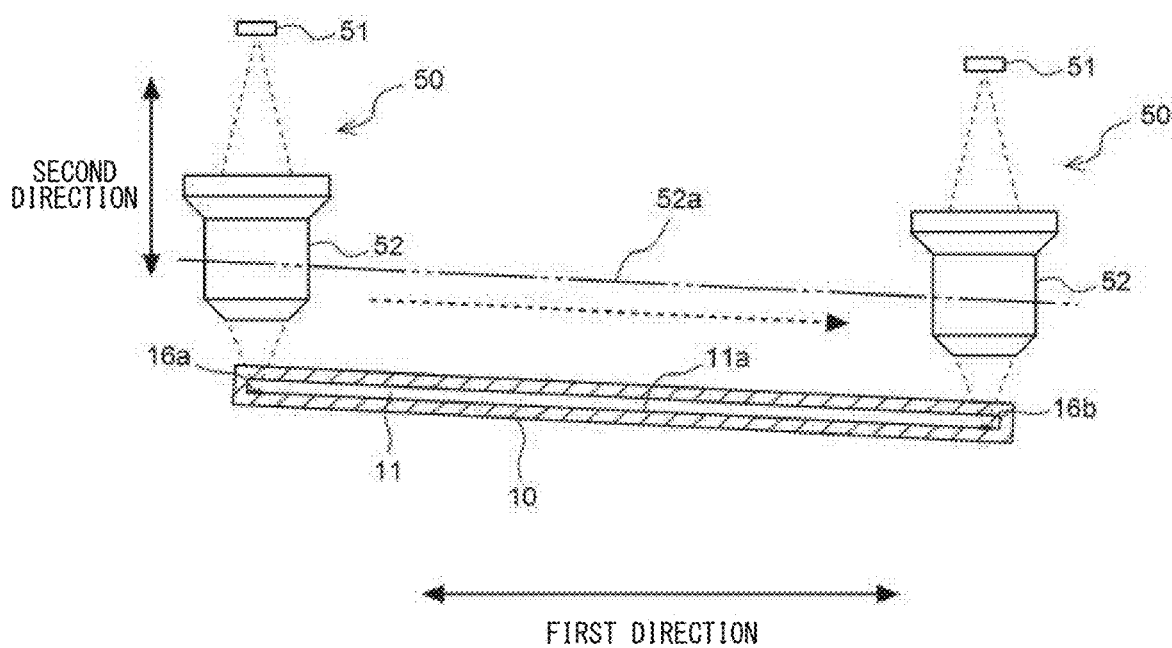
FIG. 7 is a diagram for explaining determination of a moving speed of an objective lens.

With reference to FIG. 7, determination of the moving speed of the objective lens 52 is described. As described above, the sample cell 10 is placed on the placement unit 20 so as to be inclined relative to the horizontal direction. As shown in FIG. 7, in a case where the sample cell 10 is inclined, when taking images is performed using a plurality of positions in the sample cell 10 as visual fields, the position of the objective lens 52 which allows the focal point to be on the bottom face 11a of the internal space 11 is different in each visual field. Therefore, if the sample cell 10 is horizontally moved in the first direction while the objective lens 52 is rested, the distance between the objective lens 52 and the bottom face 11a of the sample cell 10 changes. Thus, even if the focal point is on the bottom face 11a in one visual field, the focal point will not be on the bottom face 11a in another visual field. In order to cause the focal point to be on the bottom face 11a in every visual field, it is necessary to keep constant the distance between the objective lens 52 and the bottom face 11a while the sample cell 10 is moved in the first direction. That is, the position of the objective lens 52 which allows the focal point to be on the bottom face 11a of the internal space 11 is on a straight line 52a which is parallel to the bottom face 11a. The straight line 52a is a straight line that passes through the first focusing position and the second focusing position.

In the imaging operation with respect to one urine sample, taking images is performed in a plurality of visual fields of the sample cell 10. As described later, in the imaging operation, while the first drive unit 61 is moving the placement unit 20 at a uniform speed in the first direction, the imaging unit 50 performs taking images a plurality of times. Since cells in a urine sample having been introduced into the internal space 11 are located above the bottom face 11a, the cell imaging device 100 causes, in each visual field, the focal point of the objective lens 52 to be at a position that is above the bottom face 11a by a constant distance.

During the imaging operation, in order to keep the focal point of the objective lens 52 at the position above the bottom face 11a by the constant distance, the second drive unit 62 moves the imaging unit 50 at a uniform speed in the second direction. At this time, the moving speed in the first direction of the placement unit 20 and the moving speed in the second direction of the imaging unit 50 are combined together, whereby the objective lens 52 and the sample cell 10 relatively move at a uniform speed in an oblique direction. In step S106, while the placement unit 20 is moved at a uniform speed in the first direction, a moving speed at which the objective lens 52 is moved relative to the sample cell 10 along the straight line 52a is determined.

The time period from the start to the end of the imaging operation, that is, the time period in which the second drive unit 62 moves the objective lens 52 (hereinafter, referred to as "set time period") is set in advance. The set time period is also a time period in which the first drive unit 61 moves the placement unit 20. The moving speed of the objective lens 52 is the speed at which the objective lens 52 moves from the first focusing position to the second focusing position in the set time period. Specifically, the distance between the first focusing position and the second focusing position in the second direction is calculated, and the calculated distance is divided by the set time period, whereby the moving speed of the objective lens 52 is determined.

In a case where three or more reference marks are provided to the sample cell 10 so as to be distanced from one another in the first direction, the focusing position may be detected at each of the reference marks, and the moving speed may be determined from the detected three or more focusing positions.

When the controller 70 has determined the moving speed of the objective lens 52, the controller 70 stores the speed information indicating the moving speed in the memory. The speed information is information to be used in focal point adjustment in each visual field for the objective lens 52. The speed information is also information that reflects the inclination of the bottom face 11a of the internal space 11.

FIG. 6 is referred to, again. After step S106, the controller 70 ends the moving speed determination operation.

Upon ending the initialization operation, the cell imaging device 100 enters a standby state. The standby state is a state which allows reception of a urine sample.

Figure 8:
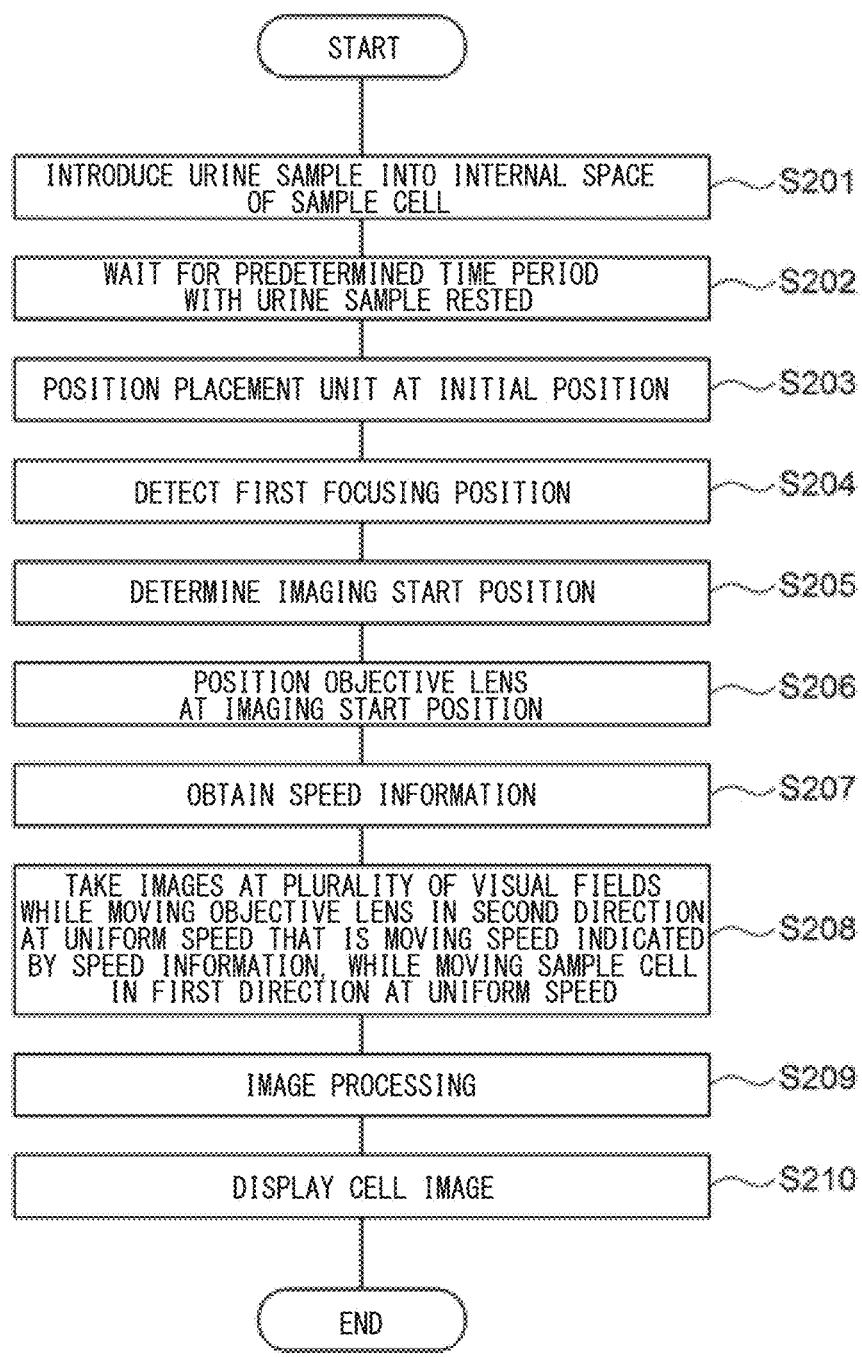
FIG. 8 is a flow chart showing the procedure of a urine sample imaging process according to Embodiment 1.

In the standby state, when the cell imaging device 100 has received from the user an instruction to start taking images for the urine sample, the cell imaging device 100 performs a urine sample imaging process. Hereinafter, with reference to FIG. 8, the urine sample imaging process is described.

In step S201, the controller 70 controls the aspiration tube 151 and the pump 152 to aspirate a predetermined amount of the urine sample from the sample container 160 and introduce the urine sample into the internal space 11 of the sample cell 10. The urine sample has no reagent such as a staining liquid or a diluent mixed therein, and has not been subjected to a centrifugation process.

In step S202, the controller 70 waits for a predetermined time period, such as 100 seconds, for example. Accordingly, the urine sample held in the sample cell 10 is left still for the predetermined time period, cells sediment in the urine sample, and many of the cells are located on the bottom face 11a of the internal space 11.

In step S203, the controller 70 controls the first drive unit 61 to move the placement unit 20 to the initial position.

In step S204, the controller 70 detects the first focusing position which is the focusing position of the objective lens 52 at the initial position. The controller 70 performs the automatic focusing operation three times in order to detect the first focusing position. Among the obtained three focusing positions, the controller 70 excludes one that has the most deviated numerical value indicative of the focusing position, and obtains the mean value of the remaining two focusing positions. The controller 70 stores in the memory the obtained mean value as the first focusing position.

The reason why the first focusing position is detected again in step S204 although the first focusing position has been detected in the moving speed determination operation is to eliminate any displacement of the focusing position that could be caused by a lapse of time. In some cases, a lapse of time causes change in the temperature of the room where the cell imaging device 100 is placed, and such a temperature change could cause change in the distance between components of the cell imaging device 100, for example, the distance between the objective lens 52 and the sample cell 10. Therefore, if the objective lens 52 is located at the first focusing position that has been detected in the moving speed determination operation, the focal point of the objective lens 52 may fail to be on the bottom face 11a due to the temperature change. Therefore, the first focusing position is detected again in step S204, to ensure the focal point of the objective lens 52 to be on the bottom face 11a of the internal space 11.

In step S205, the controller 70 obtains an imaging start position which is obtained by correcting the first focusing position to a position that is above the first focusing position by a predetermined offset amount.

Figure 9:
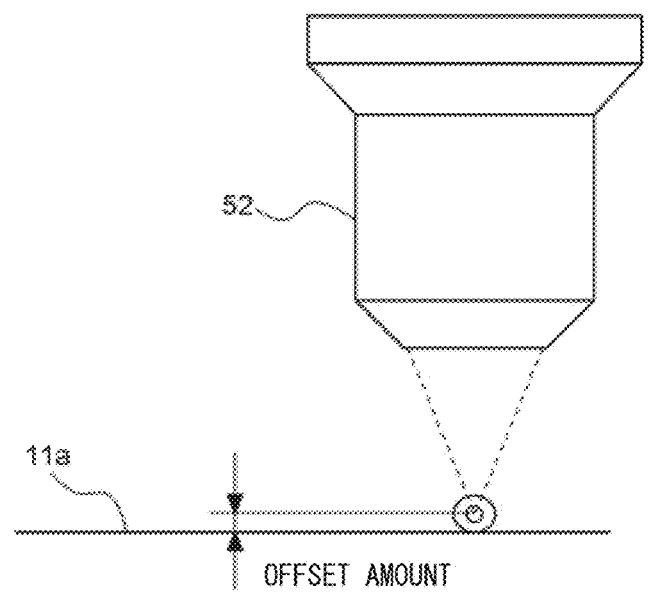
FIG. 9 is a diagram for explaining an offset amount of the objective lens.

With reference to FIG. 9, the offset amount is described. When the objective lens 52 is at the first focusing position, the focal point of the objective lens 52 is on the bottom face 11a. Since many of the cells are located on the bottom face 11a, the focal point of the objective lens 52 is not on the cells. If an image of a cell is taken in this state, an unclear image of the cell is obtained. Therefore, in order to cause the focal point of the objective lens 52 to be at the cell, the objective lens 52 is moved upwardly by about a distance corresponding to the radius of the cell, thereby locating the focal point of the objective lens 52 near the center of the cell.

The offset amount is stored by the controller 70 in advance. If the offset amount is set to, for example, 5 to 6 µm, the focal point of the objective lens 52 can be at a red blood cell. However, the offset amount may not be 5 to 6 µm. The offset amount may be set as appropriate according to the size of the cell of interest.

In a case where the first reference mark 16a and the second reference mark 16b are provided to a place other than the bottom face 1a of the internal space 11 of the sample cell 10, the offset amount may be set as the distance in the second direction from the face where the first reference mark 16a and the second reference mark 16b are provided to the center position of the cell of interest.

FIG. 8 is referred to, again. In step S206, the controller 70 controls the second drive unit 62 to locate the objective lens 52 at the imaging start position. In step S207, the controller 70 reads out speed information from the memory.

In step S208, the controller 70 performs the imaging operation. In the imaging operation, the controller 70 controls the first drive unit 61 and the second drive unit 62 to simultaneously start moving the placement unit 20 in the first direction and moving the imaging unit 50 in the second direction. The first drive unit 61 moves, without stopping, the placement unit 20 in the first direction at a set speed for a set time period. The second drive unit 62 moves, without stopping, the imaging unit 50 in the second direction at a speed indicated by the speed information for a set time period.

Figure 10:
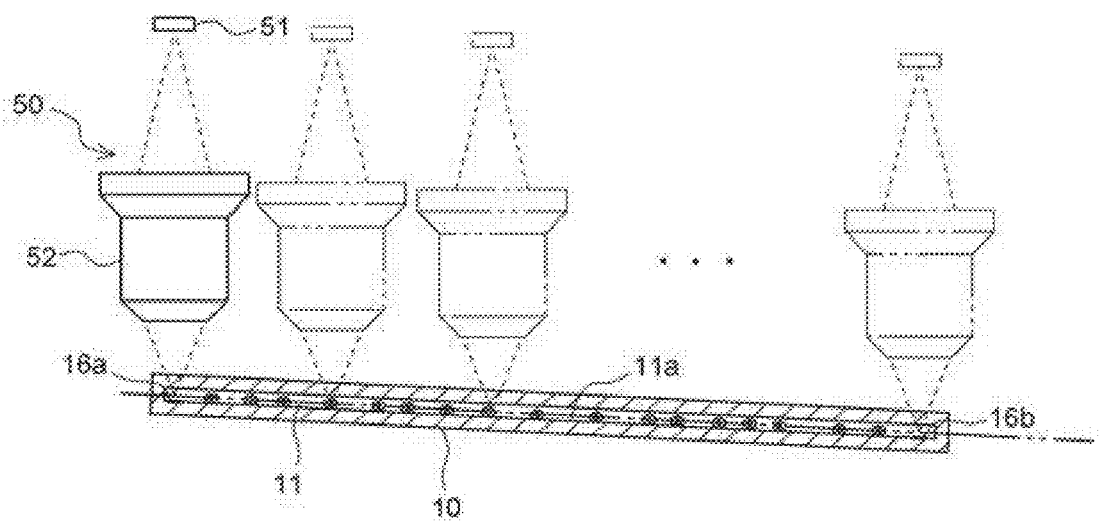
FIG. 10 is a diagram for explaining focal point adjustment of the imaging unit performed in imaging operation.

FIG. 10 is referred to. In the imaging operation, the controller 70 controls the imaging unit 50 to perform taking images a plurality of times. Associated with movement of the placement unit 20, the visual field of the objective lens 52 is moved from the first reference mark 16a to the second reference mark 16b. Thus, the imaging unit 50 performs taking images at a plurality of visual fields in a region between the first reference mark 16a and the second reference mark 16b.

While the placement unit 20 is continually moved in the first direction at the set speed, the imaging unit 50 is continually moved in the second direction at the speed indicated by the speed information. Thus, the objective lens 52 is moved relative to the sample cell 10, in parallel with the bottom face 11a of the internal space 11. That is, the objective lens 52 is moved in the second direction in accordance with the inclination of the internal space 11 of the sample cell 10. When the placement unit 20 is at the initial position, the focal point of the objective lens 52 is located above the bottom face 11a by an offset amount therefrom. Thus, the focal point of the objective lens 52 is moved on a straight line that is above the bottom face 11a by the offset amount. Therefore, while the objective lens 52 and the sample cell 10 are moving relative to each other, the focal point position of the objective lens 52 is located in the vicinity of the bottom face 11a of the internal space 11 in each visual field. As a result, the state where the focal point of the objective lens 52 is at a cell is maintained, and a clear cell image can be stably obtained. In addition, while the placement unit 20 is continually moved in the first direction at a uniform speed, the light source 41 emits pulsed light at equal intervals. Thus, without the need to stop the placement unit 20 every time an image is to be taken, it is possible to obtain an unblurred image.

In the imaging operation, focal point adjustment is performed, without detecting the focused state in each visual field and by moving the objective lens 52 at a uniform speed which is a determined moving speed. Therefore, the time period of the imaging operation can be shortened. In addition, the focal point position is not affected by the density of cells or the sizes of cells in the urine sample, and the focal point position in each visual field can be made uniform. Since images are taken while the sample cell 10 is continually moved in the first direction without being stopped, the sample cell 10 need not be stopped in order to take an image in each visual field, and vibration of cells in the liquid sample due to the stop of the sample cell 10 can be suppressed. Therefore, there is no need to wait until vibration of cells stops, and clear cell images can be stably obtained.

When a set time period has elapsed from the start of movement of the imaging unit 50 and the placement unit 20, the placement unit 20 reaches the final position. That is, the second reference mark 16b is located on the optical axis of the imaging unit 50. At this moment, the imaging unit 50 and the placement unit 20 stop and the imaging operation is completed.

In the urine sample imaging process, with respect to taking images for one urine sample, the automatic focusing operation is performed only for the detection of the first focusing position at the initial position. However, a configuration may be employed in which in the moving speed determination operation, as information for performing the focal point adjustment for each visual field, speed information indicating a determined moving speed and information indicating the detected first focusing position are stored, and in the urine sample imaging process, positioning of the objective lens 52 at the initial position is performed by using the stored information indicating the first focusing position. This configuration eliminates the need to detect the focused state at the initial position in the urine sample imaging process, and taking images for the urine sample can be performed in a still shorter time period. However, as described above, there are cases in which, due to temperature environment and the like in the facility, the first focusing position determined in the moving speed determination operation may fail to allow the focal point of the objective lens 52 to be on the bottom face 11a of the internal space 11. Therefore, from the viewpoint of obtaining a clear image in focus, it is preferable to detect the first focusing position for each urine sample.

In a case where taking images is consecutively performed for a plurality of urine sample, temperature change does not substantially occur between consecutive image-taking operations performed on urine samples because the time interval therebetween is short. Thus, a configuration may be employed in which, instead of detecting the first focusing position for each urine sample, the first focusing position is detected every plurality of urine samples, such as every 10 urine samples, for example. Accordingly, it is possible to suppress the number of times of detecting the first focusing position, while maintaining the state where the focal point is at a cell in each urine sample, thereby being able to save the time period.

In the urine sample imaging process, the automatic focusing operation may be performed at the initial position and the final position, whereby the first focusing position and the second focusing position may be detected. In this case, the controller 70 determines the moving speed of the imaging unit 50 for each urine sample. Thus, there is no need to perform the moving speed determination operation during the initialization operation. Accordingly, the inclination angle of the bottom face 11a of the internal space 11 can be accurately specified for each urine sample.

FIG. 8 is referred to, again. The image outputted as a signal from the image pickup element 51 is inputted to the controller 70 and stored. In step S209, from each image obtained by the imaging unit 50, the controller 70 performs image processing and cuts out a partial image for each cell or other particle.

Figure 11:
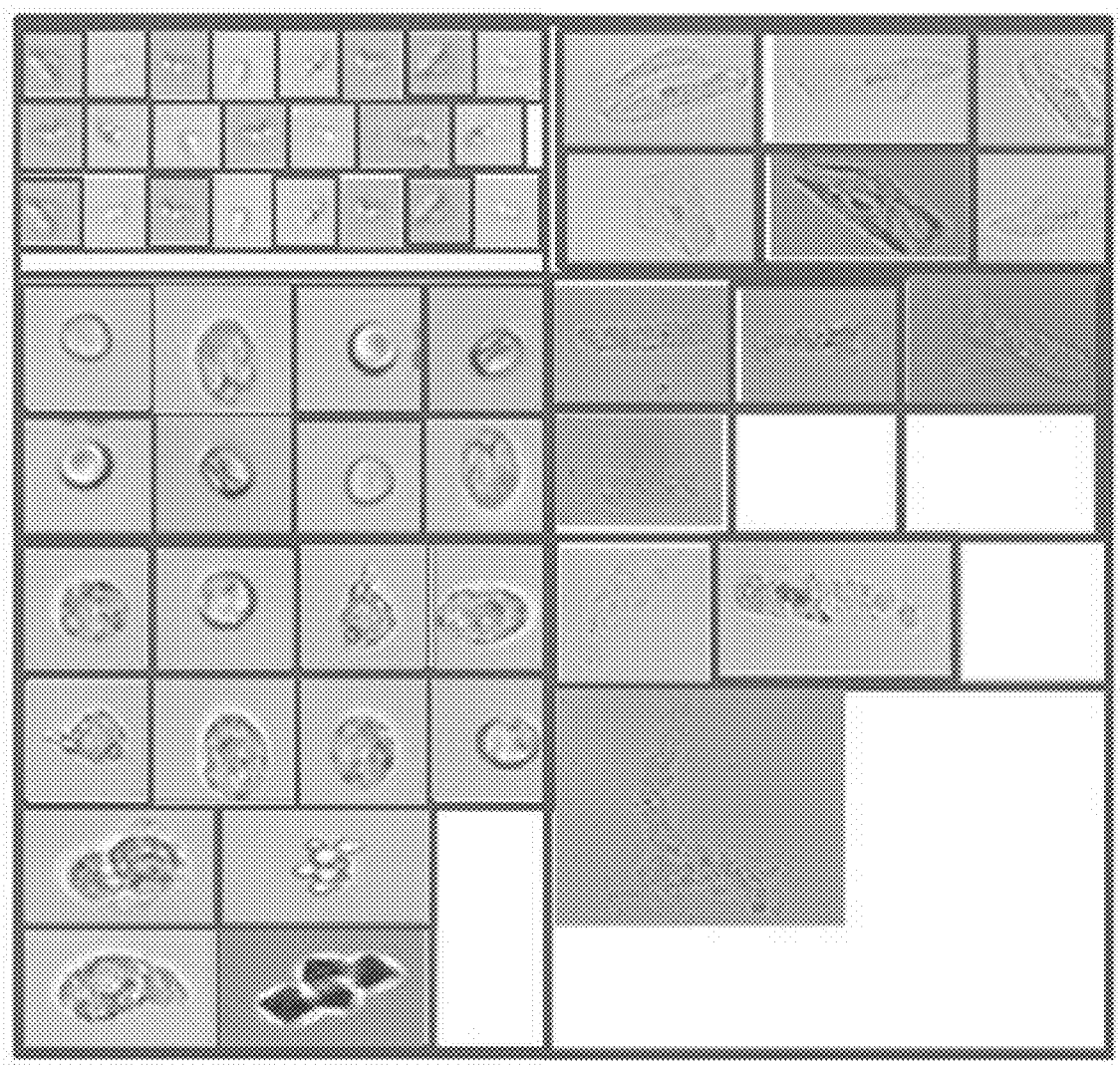
FIG. 11 is a diagram showing a display example of images of cells.

In step S210, the controller 70 causes the display unit 80 to display the cut out partial image. FIG. 11 shows a display example of images in the cell imaging device. As shown in FIG. 11, on the display unit 80, a plurality of images of cells and other particles contained in one urine sample are displayed side by side. After step S210, the controller 70 ends the urine sample imaging process.

Instead of using the first reference mark 16a and the second reference mark 16b, the relative distances among a plurality of positions in the bottom face 1a of the internal space 11 may be detected by using an optical or ultrasound-type distance sensor. Then, coordinates of each of the plurality of positions may be obtained on the basis of the detected relative distances, and then information reflecting the inclination of the sample cell 10 on the basis of the obtained coordinates may be obtained.

(Embodiment 2)

Figure 12:
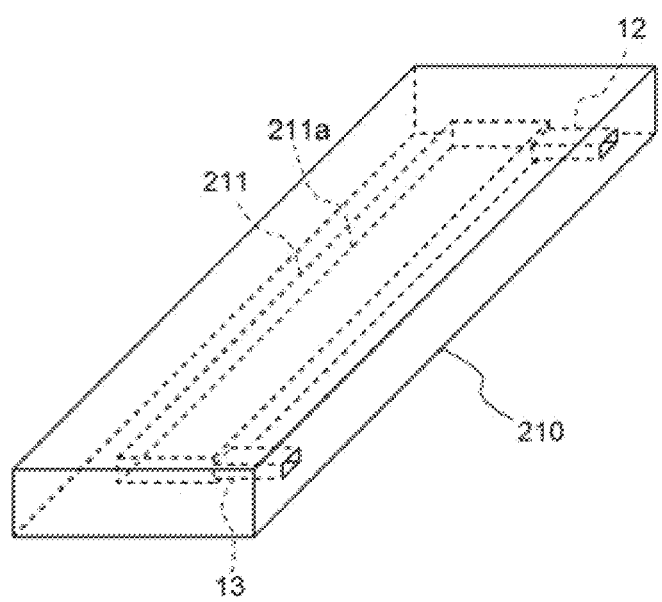
FIG. 12 is a schematic diagram showing a configuration of a sample cell according to Embodiment 2.

As shown in FIG. 12, a sample cell 210 of the cell imaging device is not provided with a reference mark on a bottom face 211a of an internal space 211. The other configurations of the cell imaging device are the same as the configurations of the cell imaging device 100 described above, and thus, description thereof is omitted.

The cell imaging device determines the moving speed by using a control sample that contains standard particles each having a set size. The standard particles contained in the control sample have a uniform size.

Figure 13:
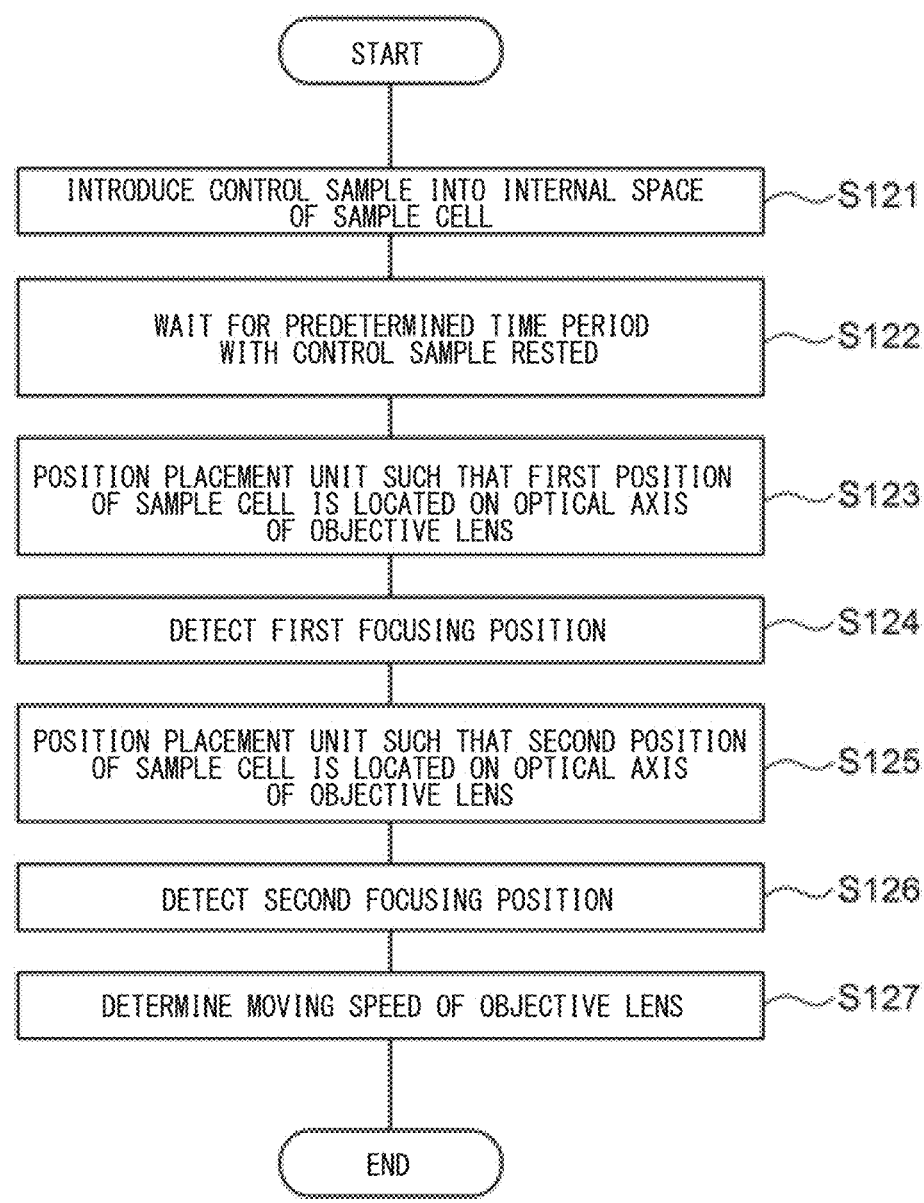
FIG. 13 is a flow chart showing the procedure of a moving speed determination operation according to Embodiment 2.

When the user activates the cell imaging device, the cell imaging device performs an initialization operation. The initialization operation includes a moving speed determination operation for determining the moving speed of the imaging unit 50 used when images of cells in urine are taken. With reference to FIG. 13, the moving speed determination operation is described.

In step S121, the controller 70 controls the aspiration tube 151 and the pump 152 to aspirate a predetermined amount of a control sample from a sample container containing the control sample and introduce the control sample into the internal space 211 of the sample cell 210.

In step S122, the controller 70 waits for a predetermined time period, such as 100 seconds, for example. Accordingly, the control sample held in the sample cell 210 is left still for the predetermined time period, standard particles sediment in the control sample, and many of the standard particles are located on the bottom face of the internal space 211.

In step S123, the controller 70 controls the first drive unit 61 to move the placement unit 20 such that a first position in the internal space 211 of the sample cell 210, such as a position to the outlet 13 side, for example, is on the optical axis of the imaging unit 50.

In step S124, the controller 70 detects a first focusing position which is the focusing position of the objective lens 52 at the first position. The controller 70 performs an automatic focusing operation three times in order to detect the first focusing position. In the automatic focusing operation, the second drive unit 62 moves the objective lens 52 in the second direction, and the focusing detection unit 71 detects a state where the focal point is at a standard particle present at the first position.

Among the obtained three focusing positions, the controller 70 excludes one that has the most deviated numerical value indicative of the focusing position, and obtains the mean value of the remaining two focusing positions. The controller 70 stores in the memory the obtained mean value as the first focusing position.

In step S125, the controller 70 controls the first drive unit 61 to move the placement unit 20 such that a second position in the internal space 211 of the sample cell 210, such as a position to the inlet 12 side, for example, is on the optical axis of the imaging unit 50.

In step S126, the controller 70 detects a second focusing position which is the focusing position of the objective lens 52 at the second position. The controller 70 performs the automatic focusing operation three times in order to detect the second focusing position.

Among the obtained three focusing positions, the controller 70 excludes one that has the most deviated numerical value indicative of the focusing position, and obtains the mean value of the remaining two focusing positions. The controller 70 stores in the memory the obtained mean value as the second focusing position.

In step S127, the controller 70 determines the moving speed of the objective lens 52 by using the first focusing position and the second focusing position. The operation in step S127 is the same as the operation in step S106, and thus, description thereof is omitted. After step S127, the controller 70 ends the moving speed determination operation.

Upon ending the initialization operation, the cell imaging device 200 enters a standby state. The standby state is a state which allows reception of a urine sample.

Figure 14:
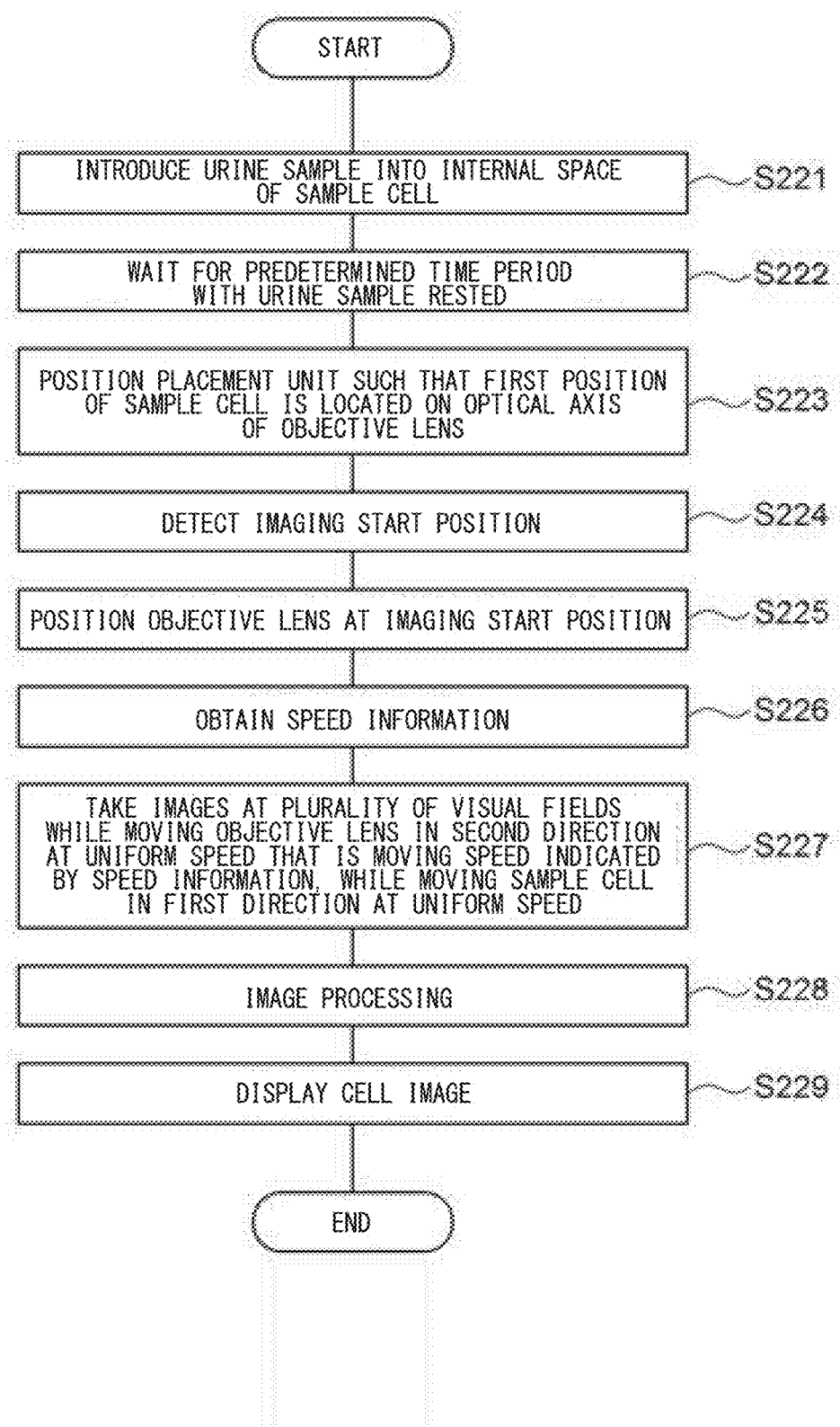
FIG. 14 is a flow chart showing the procedure of a urine sample imaging process according to Embodiment 2.

In the standby state, when the cell imaging device 200 has received from the user an instruction to start taking images for the urine sample, the cell imaging device 200 performs a urine sample imaging process. Hereinafter, with reference to FIG. 14, the urine sample imaging process is described.

In step S221, the controller 70 controls the aspiration tube 151 and the pump 152 to aspirate a predetermined amount of the urine sample from the sample container 160 and introduce the urine sample into the internal space 11 of the sample cell 10. The urine sample has no reagent such as a staining liquid or a diluent mixed therein, and has not been subjected to a centrifugation process.

In step S222, the controller 70 waits for a predetermined time period, such as 100 seconds, for example. Accordingly, the urine sample held in the sample cell 210 is left still for the predetermined time period, cells sediment in the urine sample, and many of the cells are located on the bottom face of the internal space 211.

In step S223, the controller 70 controls the first drive unit 61 to move the placement unit 20 such that the first position in the internal space 211 of the sample cell 210 is on the optical axis of the imaging unit 50.

In step S224, the controller 70 detects an imaging start position which is the focusing position of the objective lens 52 at the first position. The controller 70 performs the automatic focusing operation three times in order to detect the imaging start position. In each automatic focusing operation, the focusing detection unit 71 detects a state where the focal point is at a cell present at the first position. Among the obtained three focusing positions, the controller 70 excludes one that has most deviated numerical value, and obtains the mean value of the remaining two focusing positions. The controller 70 stores in the memory the obtained mean value as the imaging start position.

In step S225, the controller 70 controls the second drive unit 62 to locate the objective lens 52 at the imaging start position. In step S226, the controller 70 reads out speed information from the memory. Since the imaging start position is the position where the focal point is at a cell, there is no need to perform correction using an offset amount.

In step S227, the controller 70 performs an imaging operation. The operation in step S227 is the same as the operation in step S208, and thus, description thereof is omitted.

In step S228, from each image obtained by the imaging unit 50, the controller 70 performs image processing and cuts out a partial image for each cell or other particle.

In step S229, the controller 70 causes the display unit 80 to display the cut out partial image. After step S229, the controller 70 ends the urine sample imaging process.

(Embodiment 3)

Figure 15:
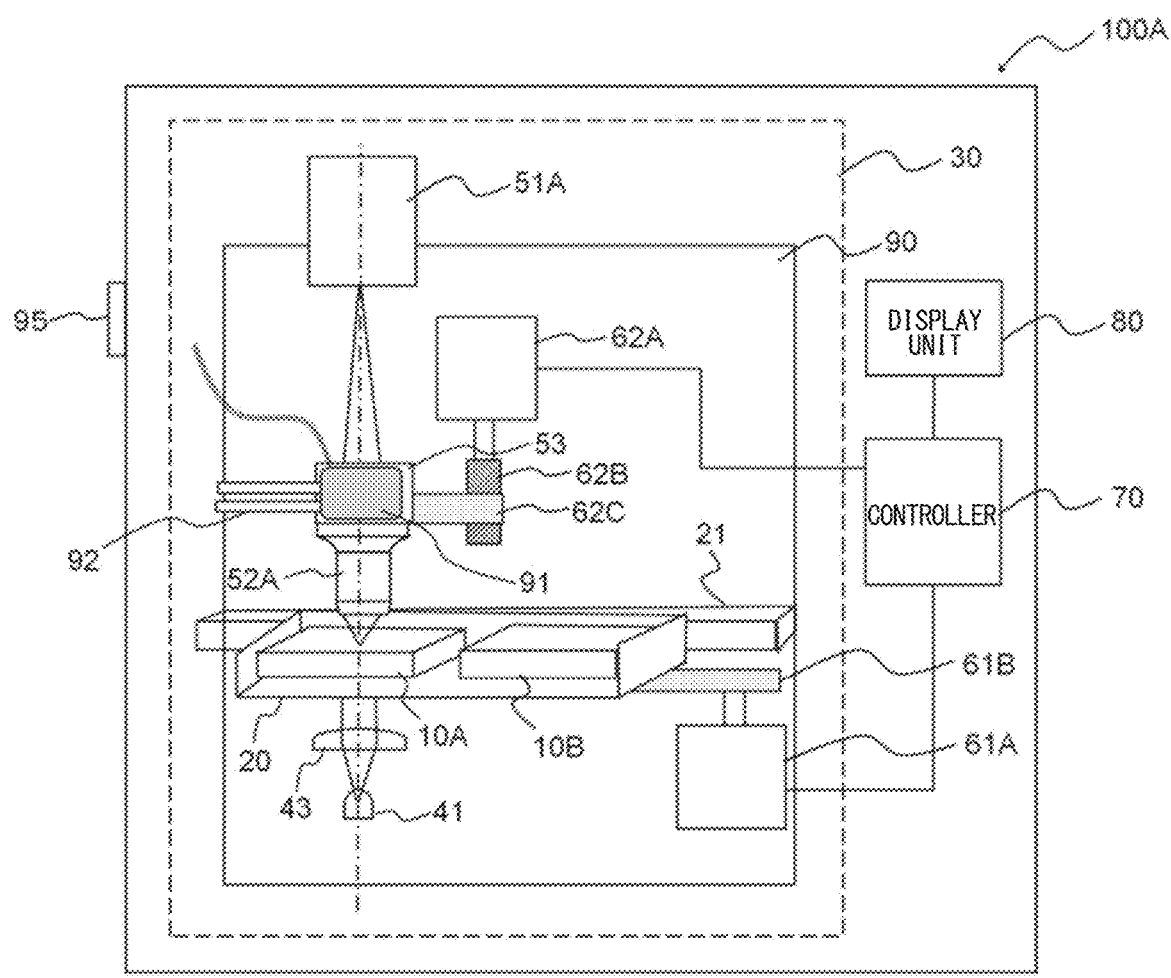
FIG. 15 is a schematic diagram showing a configuration of a cell imaging device according to Embodiment 3.

With reference to FIG. 15, another embodiment of the cell imaging device is described. A cell imaging device 100A according to Embodiment 3 is configured to perform temperature control for suppressing focal point displacement of the objective lens due to temperature change. Description of the same configurations as those of Embodiment 1 is omitted.

Figure 16:
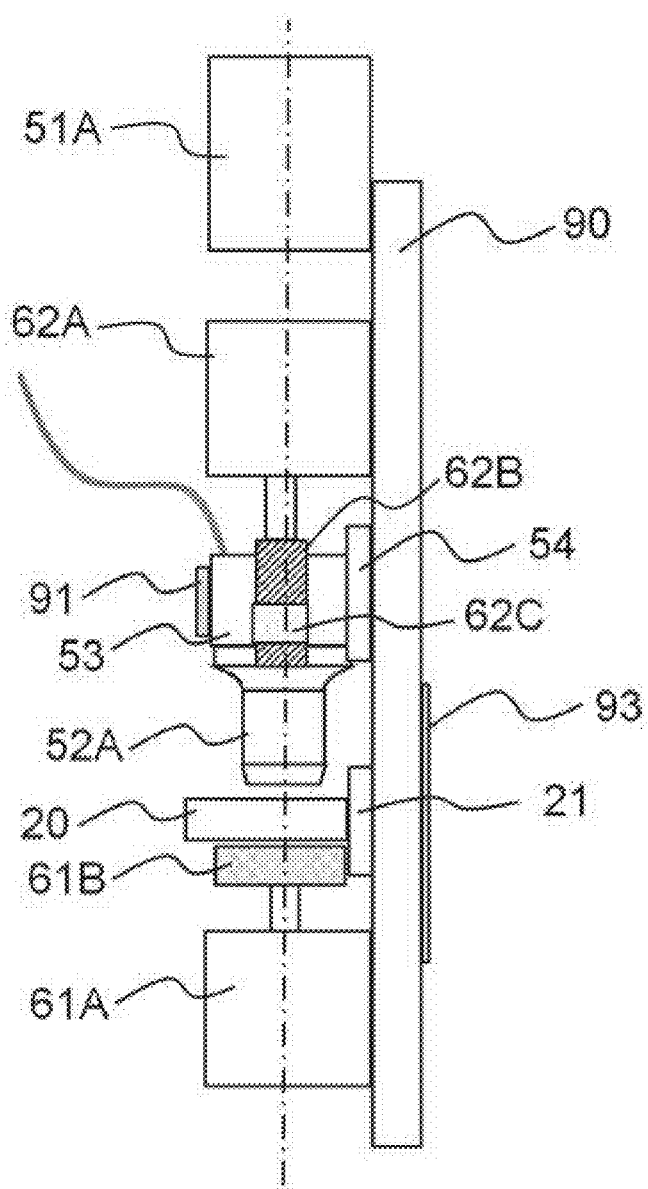
FIG. 16 is a side view showing an imaging mechanism of the cell imaging device according to Embodiment 3.

The cell imaging device 100A includes as the imaging unit: an objective lens 52A; a lens block 53 which is a lens holder that holds the objective lens 52A; and an image pickup element 51A provided so as to be spaced away from the lens block 53. The lens block 53 has a hollow cubic shape. The lower face of the lens block 53 is provided with a hole into which an upper end portion of the objective lens 52A can be inserted, whereby the lens block 53 is configured to be able to hold the objective lens 52A inserted through the hole. As shown in FIG. 16, the lens block 53 is mounted to a linear slider 54, and is configured to be movable along the linear slider 54 in the second direction which is the optical axis direction. The lens block 53 is configured to move in the optical axis direction along the linear slider 54 when a pulley 62B and a belt 62C are driven by an electric motor 62A. The electric motor 62A is a stepping motor. The image pickup element 51A and the linear slider 54 are fixed to a base block 90 which is a base plate, and the lens block 53 is moved in the optical axis direction relative to the image pickup element 51. Compared with a case where the lens barrel holding the image pickup element and the objective lens is moved in the optical axis direction as in the cell analyzer 100 of Embodiment 1, since the weight of the member that is moved in the optical axis direction is reduced, the electric motor 62A, the pulley 62B, and the belt 62C which serve as a drive mechanism can be downsized.

As shown in FIG. 15, the placement unit 20 is mounted to a linear slider 21. The placement unit 20 is placed in the horizontal direction. The linear slider 21 is fixed to the base block 90 such that the linear slider 21 is inclined by a predetermined toward the vertical direction relative to the horizontal direction. The inclination angle of the linear slider 21 is very small, and thus, the linear slider 21 is fixed to the base block 90 in a substantially horizontal direction. When a belt 61B is driven by an electric motor 61A, the placement unit 20 is moved in a substantially horizontal direction along the linear slider 21. Two sample cells 10A, 10B are fixed to the placement unit 20. When the placement unit 20 is moved, the sample cells 10A, 10B are also moved integrally with the placement unit 20. Since taking images for a plurality of urine samples can be performed in parallel by use of the two sample cells 10A, 10B, the imaging process can be efficiently performed.

A heater 91 for performing temperature control of the objective lens 52A is mounted to the lens block 53. The heater 91 is a rubber heater. The heater 91 is mounted to the entirety of one lateral face of the lens block 53, and is configured to heat the lens block 53. A thermistor 92 is mounted to the lens block 53, and the temperature of the lens block 53 is detected by the thermistor 92. Instead of the thermistor 92, a thermocouple may be used as a temperature sensor. The lens block 53 is formed from aluminium having a high thermal conductivity. By the lens block 53 being heated by the heater 91, air inside the lens block 53 is warmed, and the warmed air reaches the objective lens 52A. The objective lens 52A includes a lens part and a tubular part surrounding the lens part. The air warmed in the lens block 53 enters the tubular part of the objective lens 52A, whereby the temperature of the lens part is controlled. It is sufficient that the lens block 53 is formed from a material having a high thermal conductivity, and may be formed from copper. The heater 91 is provided to the lens block 53 which has a wider surface area than the objective lens 52A, and thus, even in a case where the surface area of the objective lens 52A is too small to provide a heater thereto, temperature control of the objective lens 52A can be effectively performed.

Figure 17:
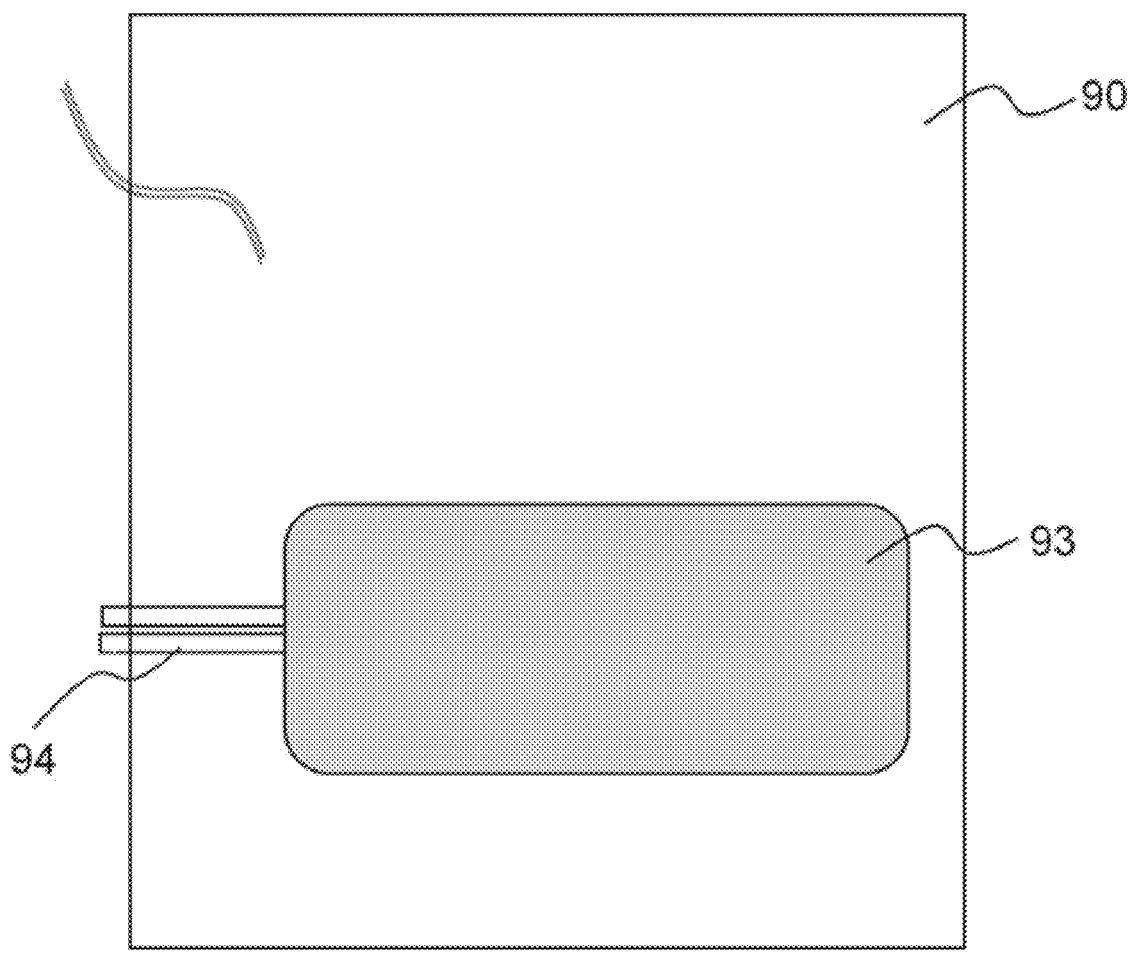
FIG. 17 is a rear view showing a base block according to Embodiment 3.

As shown in FIG. 16, the image pickup element 51A, the electric motor 61A, the electric motor 62A, the linear slider 54, and the linear slider 21 are fixed to the base block 90. With respect to the base block 90, a heater 93 for performing temperature control of the base block 90 is mounted to the face thereof that is opposite to the face where the image pickup element 51A and the like are mounted. The heater 93 is also a rubber heater, and is configured to heat the base block 90. As shown in FIG. 17, a thermistor 94 is mounted to the base block 90, and the temperature of the base block 90 is detected by the thermistor 94. Instead of the thermistor 94, a thermocouple may be used as a temperature sensor. The base block 90 is formed from aluminium having a high thermal conductivity. It is sufficient that the base block 90 is formed from a material having a high thermal conductivity, and the base block 90 may be formed from copper, for example.

As shown in FIG. 15, the base block 90, the image pickup element 51A, the lens block 53, the objective lens 52A, the placement unit 20, the electric motors 61A, 62A, and the like are disposed in a housing 30. In addition, a cell analyzer 100A has mounted thereto a temperature sensor 95 for detecting the ambient temperature outside the device.

Figure 18:
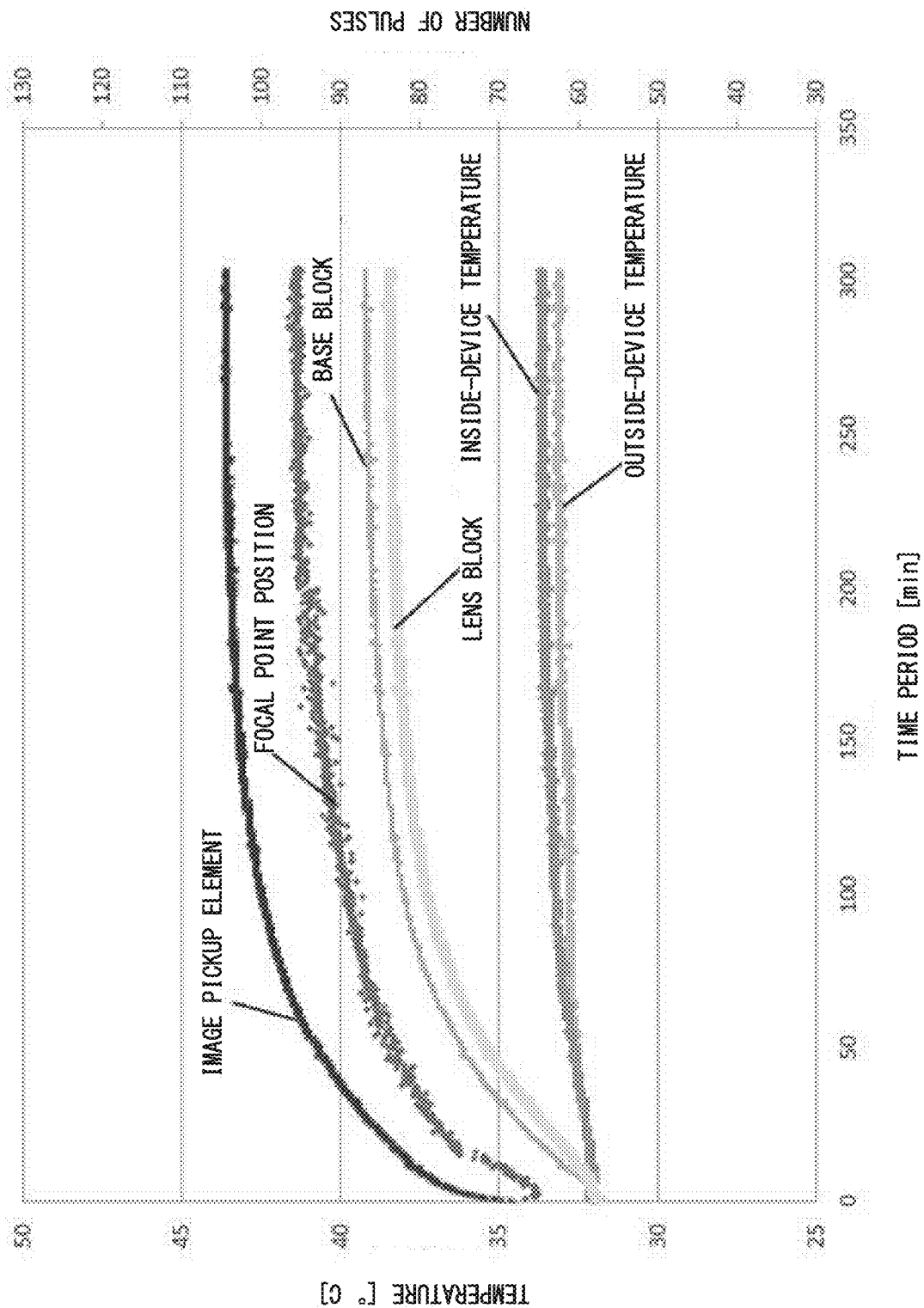
FIG. 18 is a graph showing change in the focal point position of the objective lens when no heater was provided to a lens block and the base block according to Embodiment 3.

In a case where the objective lens 52A is used in an environment in which temperature change occurs, there is a risk of occurrence of focal point displacement because the lens part of the objective lens 52A expands or contracts associated with the temperature change. For example, while the cell imaging operation is performed after activation of the cell imaging device 100A, the image pickup element 51A generates heat and the temperature is increased. If heat generated by the image pickup element 51A is conducted to the objective lens 52A, the temperature of the objective lens 52A itself increases due to the heat, thus leading to a risk of occurrence of focal point displacement. FIG. 18 is a graph showing change in the focal point position of the objective lens 52A in a case where the heaters are not provided to the lens block 53 and the base block 90. This graph shows the result of an experiment in which the ambient temperature of the cell analyzer 100A was 32° C. As shown in this graph, while the imaging operation is performed after activation of the device, the temperature of the image pickup element 51A increases and the temperature of the lens block 53 also increases, accordingly. The "number of pulses" at the vertical axis on the right side of the graph shown in FIG. 18 indicates the number of drive pulses provided to the motor 62A in order to adjust the objective lens 52A from the origin position thereof to a predefined focal point position. As shown in the graph, as the temperature of the lens block 53 increases, the focal point position of the objective lens 52A is displaced, and the number of drive pulses for adjusting the objective lens 52A to the predefined focal point position increases. In this experiment, change as great as about 25 pulses occurred from the activation of the device until the stabilization of the focal point position of the objective lens 52A. In addition, it took 200 minutes or longer until the temperature of the lens block 53 was stabilized after the activation of the device, and thus, it took a long time for the focal point position of the objective lens 52A to be stabilized. Therefore, until the focal point position of the objective lens 52A is stabilized, it is necessary to perform focal point adjustment of the objective lens 52A every time a new urine sample is introduced into a sample cell, and thus, the imaging operation takes time.

In Embodiment 3, the heater 91 is mounted to the lens block 53 holding the objective lens 52A, and the temperature of the lens block 53 is controlled to be constant by the heater 91. Specifically, the temperature of the lens block 53 is controlled at 41° C. Since the heat of the heater 91 is conducted via the lens block 53 to the objective lens 52A, the temperature of the objective lens 52A is also kept constant. Thus, temperature change of the objective lens 52A is suppressed, whereby occurrence of focal point displacement can be suppressed.

The temperature of the objective lens 52A is affected not only by the heat from the image pickup element 51A but also by the ambient temperature of the cell imaging device 100A in some cases. In Embodiment 3, the heater 93 is also mounted to the base block 90, and the temperature of the base block 90 is controlled to be constant. The temperature of the base block 90 is controlled so as to be the same as the temperature of the lens block 53, and is specifically controlled at 41° C. The base block 90 is disposed in the housing 30, and air circulation into and out of the housing 30 is blocked. Thus, the temperature of the air in the housing 30 can be maintained at substantially the same temperature as the base block 90, whereby temperature change can be suppressed. Accordingly, the temperature of the air around the objective lens 52A disposed in the housing 30 can be maintained at substantially the same temperature as the base block 90, and thus, influence of change in the ambient temperature of the cell imaging device 100A can be suppressed, and the focal point displacement of the objective lens 52A can be further suppressed.

Since the lens block 53 holding the objective lens 52A is disposed so as to be spaced away from the image pickup element 51A, thermal conduction therebetween can be suppressed from occurring. Thus, heat generated by the image pickup element 51A is suppressed from being conducted to the objective lens 52A, whereby occurrence of focal point displacement due to increase in the temperature of the objective lens 52A can be further prevented.

Figure 19:
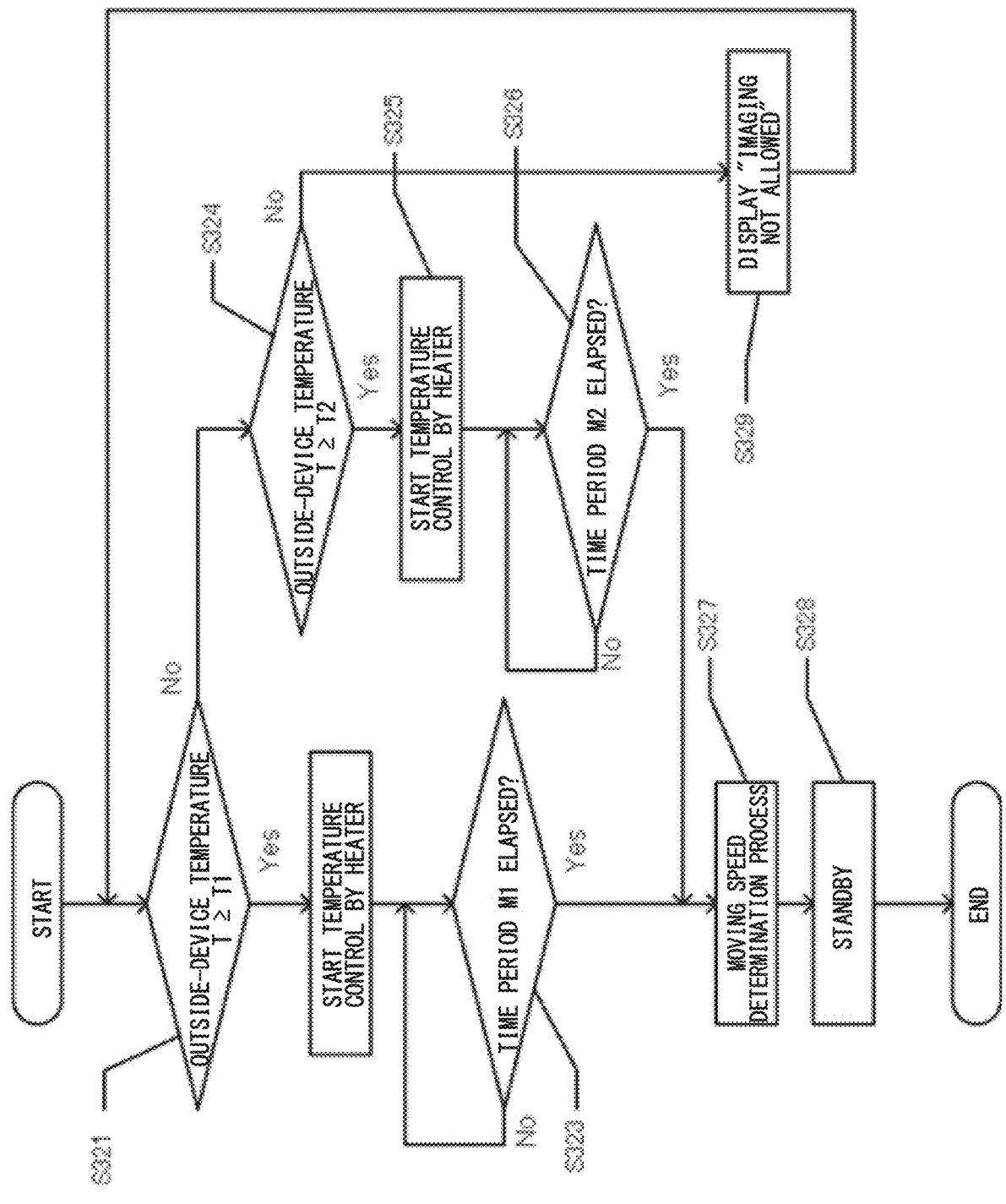
FIG. 19 is a flow chart showing an initialization operation performed at the time of activation of a cell analyzer according to Embodiment 3.
Figure 20:
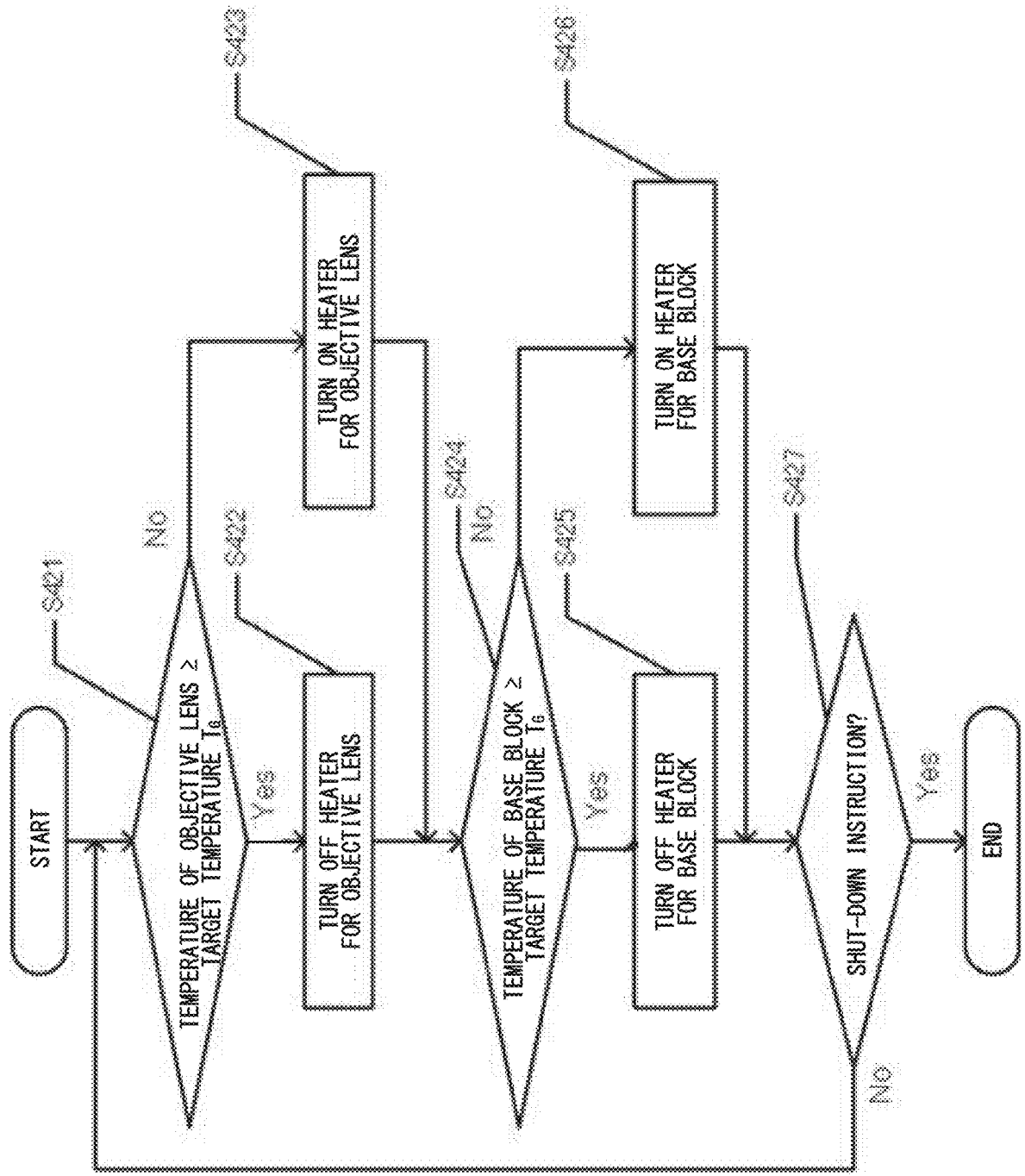
FIG. 20 is a flow chart of a temperature control process according to Embodiment 3.

With reference to FIG. 19 and FIG. 20, an operation procedure of the cell analyzer 100A is described. FIG. 19 is a flow indicating an initialization operation performed at the time of activation of the cell analyzer 100A. Upon activation of the cell analyzer 100A, in step S321, the controller 70 determines, on the basis of a detection result from the temperature sensor 95, whether an outside-device temperature T, i.e., the temperature in the room where the cell analyzer 100A is placed, is higher than or equal to T1. The temperature T1 is 15° C., for example, but may be another temperature. When the outside-device temperature T is higher than or equal to T1, the controller 70 starts in step S322 temperature control by means of the heaters 91, 93, and then, determines in step S323 whether a time period M1 has elapsed. The time period M1 is 15 minutes, for example, but may be another time period. When the time period M1 has elapsed, the controller 70 performs a moving speed determination operation in step S327. The moving speed determination operation is the same as the operation described with reference to FIG. 6. After the moving speed determination operation, the controller 70 shifts to a standby state in step S328.

When the outside-device temperature T is lower than T1, the controller 70 determines in step S324 whether the outside-device temperature T is higher than or equal to T2. The temperature T2 is 10° C., for example, but may be another temperature that is lower than the temperature T1. When the outside-device temperature T is higher than or equal to T2, the controller 70 starts in step S325 temperature control by means of the heaters 91, 93, and then determines in step S326 whether a time period M2 has elapsed. The time period M2 is 25 minutes, for example, but may be another time period that is longer than the time period M1. When the time period M2 has elapsed, the controller 70 performs the moving speed determination operation in step S327, and shifts to a standby state in step S328. In this manner, if the ambient temperature of the cell analyzer 100A is high, the time period up to shifting to a standby state is shortened, and if the ambient temperature is low, the time period up to shifting to a standby state is made long. By changing the time period up to shifting to a standby state in accordance with the ambient temperature of the cell analyzer 100A, it is possible to reliably set the temperature of the objective lens 52A to a target temperature even when the ambient temperature is low.

When the outside-device temperature T is lower than T2, the controller 70 causes in step S329 the display unit 80 to display "imaging not allowed", and returns to step S321 without shifting to a standby state. When the ambient temperature of the cell analyzer 100A is too low relative to a normally expected temperature, even if temperature control by means of the heaters 91, 93 is performed, focal point displacement of the objective lens 52A could occur. Therefore, in such a case, taking images of poor accuracy can be prevented from being performed, by prohibiting the imaging operation.

Next, with reference to FIG. 20, a temperature control process performed by the heaters 91, 93 is described. The temperature control process is continued until a shut-down instruction is received after the temperature control process is started in step S322 or step S325. Upon the start of the temperature control process, in step S421, the controller 70 determines, on the basis of a detection result from the thermistor 92, whether the temperature of the lens block 53, i.e., the temperature of the objective lens 52A, is higher than or equal to a target temperature $T_G$. The target temperature $T_G$ is 41° C., for example. When the temperature of the objective lens 52A is lower than the target temperature $T_G$, the controller 70 turns on the heater 91 in step S423. When the temperature of the objective lens 52A is higher than or equal to the target temperature $T_G$, the controller 70 turns off the heater 91 in step S422.

Subsequently, in step S424, the controller 70 determines, on the basis of a detection result from the thermistor 94, whether the temperature of the base block 90 is higher than or equal to the target temperature $T_G$. The target temperature $T_G$ is 41° C., for example. When the temperature of the base block 90 is lower than the target temperature $T_G$, the controller 70 turns on the heater 93 in step S426. When the temperature of the base block 90 is higher than or equal to the target temperature $T_G$, the controller 70 turns off the heater 93 in step S425.

In step S427, the controller 70 determines whether a shut-down instruction has been received. When the shut-down instruction has not been received, the controller 70 repeats the processes of step S421 to S426. Thus, the operation is repeated in which: when the temperatures of the objective lens 52A and the base block 90 reach the target temperature $T_G$, their corresponding heaters are turned off; and when the temperatures of the objective lens 52A and the base block 90 become lower than the target temperature $T_G$, their corresponding heaters are turned on. Accordingly, the temperatures of the objective lens 52A and the base block 90 can be maintained at temperatures close to the target temperature $T_G$.

Figure 21:
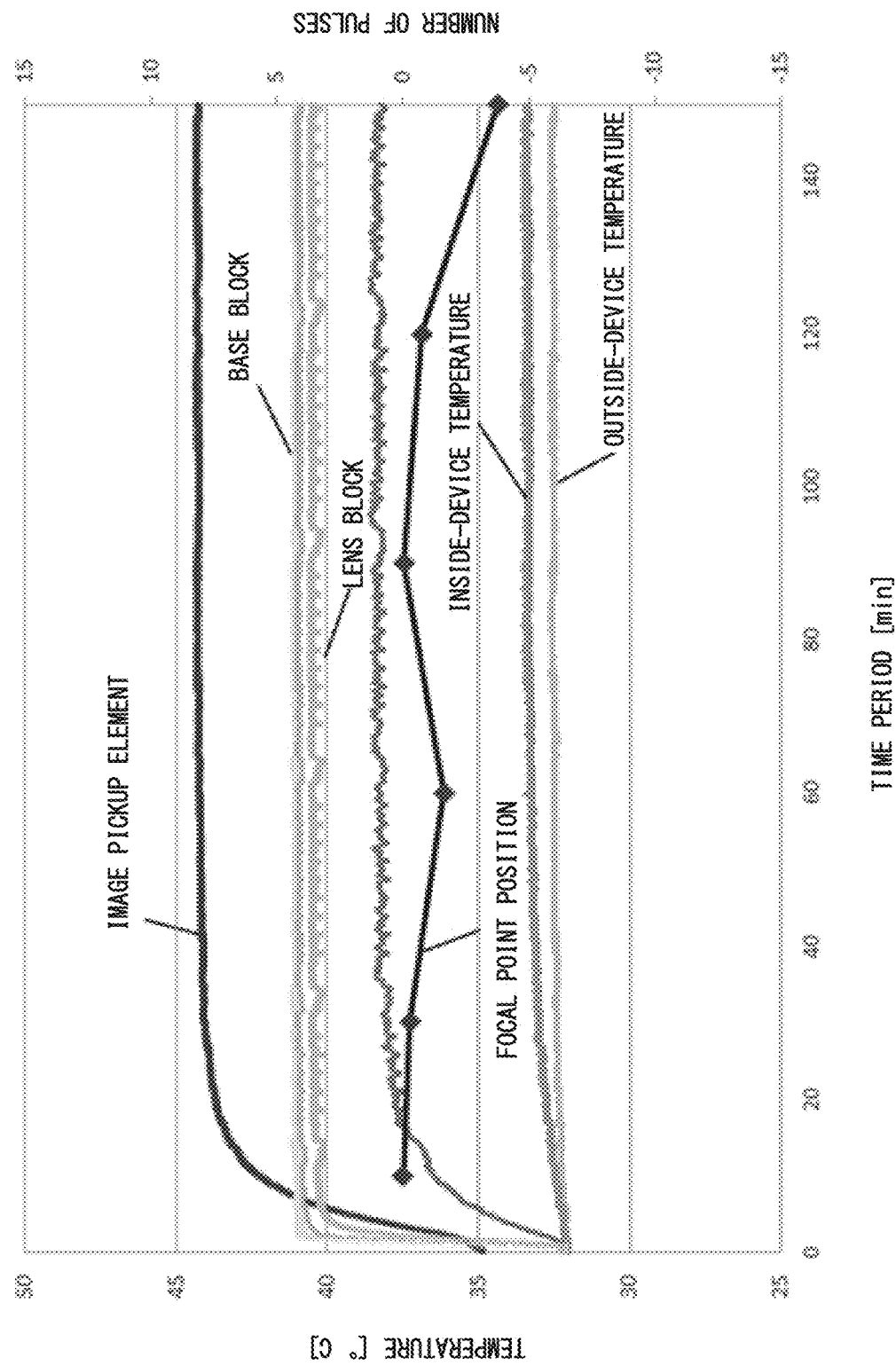
FIG. 21 is a graph showing change in the focal point position of the objective lens when temperature control was performed according to Embodiment 3.

With reference to FIG. 21, a result of an experiment is described in which temperature control by means of the heaters 91, 93 was performed. This experiment was performed under a condition of: the ambient temperature of the cell analyzer 100A being 32° C.; and the set temperature of the heaters 91, 93 being 41° C. As shown in the graph in FIG. 21, upon activation of the cell analyzer 100A, the temperature of the image pickup element 51A increases due to heat generation. However, since the base block 90 is heated by the heater 93, the difference in temperature between the base block 90 and the image pickup element 51A is reduced compared with a case shown in FIG. 18. Accordingly, heat transfer from the image pickup element 51A to the base block 90 is suppressed, the temperature of the image pickup element 51A is stabilized soon, and the temperature of the base block 90 is stabilized soon at 41° C. In the experiment shown in FIG. 21, the temperatures of the base block 90 and the lens block 53 are stabilized at 41° C. in about 10 minutes. As shown in the graph, while the temperature of the lens block 53 is stable, substantially no displacement of the focal point position of the objective lens 52A occurred. When the focal point position of the objective lens 52A at the lapse of about 15 minutes after the activation of the device is used as the reference, the displacement of the focal point position of the objective lens 52A is within 5 pulses, and the width of the change in the focal point position has been greatly reduced compared with the case shown in FIG. 18. Thus, when the temperature control by means of the heaters 91, 93 is performed, the focal point position of the objective lens 52A can be quickly stabilized. Thus, after the focal point position has been stabilized, the frequency of performing the focal point adjustment of the objective lens 52A can be reduced, and the imaging process can be efficiently performed. For example, it is possible to also reduce the number of times of performing the focal point adjustment every time images of a new urine sample are to be taken, and thus, it is possible to quickly perform the imaging process.

The target temperature for the base block 90 and the lens block 53 may not be 41° C. However, the target temperature is preferably a temperature higher than the ambient temperature of the cell analyzer 100A, and is preferably a temperature higher than, for example, 25° C. which is generally considered as room temperature in the technical field of the present invention. If the target temperature is made closer to the temperature of the image pickup element 51A, the temperatures of the base block 90 and the lens block 53 can be quickly stabilized, accordingly. However, if the target temperature is too high, the cells in the urine sample in the sample cell 10A, 10B might be influenced. Thus, it is particularly preferable that the target temperature is higher than or equal to 38° C. and lower than 42° C.

It should be noted that the embodiment disclosed herein is merely illustrative in all aspects and should not be construed as being restrictive. The scope of the present invention is defined not by the description of the above embodiment but by the scope of the claims, and includes meaning equivalent to the scope of the claims and all modifications within the scope.

What is claimed is:

1. A cell imaging device comprising:
    a sample cell at an angle with respect to a horizontal axis and including an internal space for holding a liquid sample containing cells;
    an imaging unit comprising an objective lens and configured to take images of cells contained in the liquid sample held in the internal space;
    a first drive unit configured to move the sample cell in a first direction;
    a second drive unit configured to move the objective lens in a second direction that is different from the first direction; and
    a controller configured to control the first drive unit and the second drive unit to continuously move the sample cell and the imaging unit in the first and second directions respectively at a constant speed, thereby seamlessly moving the objective lens through a plurality of imaging positions, and the controller is further configured to control the imaging unit during the movement to take images of cells contained in the liquid sample held in the internal space at the plurality of imaging positions, while continuously moving the sample cell and the imaging unit in the first and second directions, respectively.

2. The cell imaging device of claim 1, wherein the sample cell comprises a bottom face configured to support the liquid sample in the internal space.

3. The cell imaging device of claim 2, comprising a detection unit configured to detect position information regarding a position of the sample cell, wherein the controller is configured to, before the liquid sample is introduced into the sample cell, cause the detection unit to detect position information regarding each of a plurality of positions of the sample cell, and is configured to obtain the information reflecting an inclination of the bottom face on the basis of a result of the detection.

4. The cell imaging device of claim 2, further comprising a placement unit on which the sample cell is placed such that the bottom face is inclined relative to the first direction, wherein the first drive unit is configured to move the placement unit in the first direction.

5. The cell imaging device of claim 1, wherein the controller is configured to control the first drive unit and the second drive unit such that the objective lens is moved in the second direction while the sample cell is moved in the first direction, so that a focal point position of the objective lens is located in a vicinity of the bottom face of the internal space at each of the plurality of imaging positions.

6. The cell imaging device of claim 1, wherein the controller is configured to control the first drive unit and the second drive unit such that the objective lens is continually moved in the second direction while the sample cell is continually moved in the first direction without being stopped.

7. The cell imaging device of claim 1, wherein the internal space of the sample cell is elongated in the first direction.

8. The cell imaging device of claim 1, wherein the liquid sample is a urine sample.

9. The cell imaging device of claim 1, further comprising:
    a heater configured to control a temperature of the objective lens; and
    a lens holder configured to hold the objective lens, the heater coupled to the lens holder.

10. The cell imaging device of claim 9, wherein the imaging unit comprises an image pickup element fixed at a predetermined position, and the second drive unit is configured to move the lens holder in the second direction relative to the image pickup element.

11. The cell imaging device of claim 9, further comprising:
    a base plate to which the imaging unit and the sample cell are mounted;
    a housing configured to house the imaging unit, the sample cell, and the base plate; and
    a second heater configured to perform temperature control of the base plate.

12. The cell imaging device of claim 1, further comprising a pulsed-light-emitting light source configured to apply light to cells contained in the liquid sample held in the internal space of the sample cell.

13. A cell imaging method comprising:
    introducing a liquid sample containing cells into an internal space of a sample cell that is arranged with an angle with respect to a horizontal axis;
    continuously moving the sample cell and an objective lens in first and second directions respectively at a constant speed, thereby seamlessly moving the objective lens through a plurality of imaging positions; and
    taking, at the plurality of imaging positions, images of cells contained in the liquid sample held in the internal space, while continuously moving the sample cell and the objective lens in the first and second directions, respectively.

14. A cell imaging device comprising:
a sample cell including an internal space for holding a liquid sample containing cells, wherein the sample cell further includes a first reference mark and a second reference mark which are distanced from each other;
an imaging unit comprising an objective lens and configured to take images of cells contained in the liquid sample held in the internal space;
a first drive unit configured to move the sample cell in a first direction;
a second drive unit configured to move the objective lens in a second direction that is different from the first direction; and
a controller configured to:
determine a first focusing position that defines a relative position of the sample cell and the objective lens, wherein at the first focusing position the objective lens focuses with respect to the first reference mark;
determine a second focusing position that defines a relative position of the sample cell and the objective lens, wherein at the relative position the objective lens focuses with respect to the second reference mark;
control the first drive unit and the second drive unit to continuously move the sample cell and the objective lens in the first and second directions, respectively, thereby changing the relative position of the sample cell and the objective lens from the first focusing position to the second focusing position without stopping; and
control the imaging unit to take, at a plurality of imaging positions between the first and second focusing positions, images of cells contained in the liquid sample held in the internal space, while continuously moving the sample cell and the objective lens in the first and second directions, respectively.

15. The cell imaging device of claim 14, wherein the controller is configured to control the first drive unit and the second drive unit to keep the sample cell and the objective lens in a constant speed moving from the first focusing position to the second focusing position.

16. The cell imaging device of claim 14, wherein the controller is configured to control the first drive unit and the second drive unit to move the objective lens relatively along a straight line connecting the first focusing position and the second focusing position.

17. The cell imaging device of claim 14, wherein the sample cell includes an inlet for receiving the liquid sample into the internal space, and an outlet for discharging the liquid sample from the internal space,
the first reference mark is proximate to an inlet side in the internal space, and
the second reference mark is proximate to an outflow side in the internal space.

18. The cell imaging device of claim 14, wherein the sample cell comprises a bottom face configured to support the liquid sample in the internal space, and each of the first reference mark and the second reference mark is a minute groove formed in the bottom face of the internal space.

19. A cell imaging method comprising:
detecting a first focusing position that defines a relative position of a sample cell and an objective lens, wherein at the first focusing position of the objective lens focuses with respect to a first reference mark of the sample cell, and wherein the sample cell is movably arranged in a first direction and the objective lens is movably arranged in a second direction that is different from the first direction,
detecting a second focusing position that defines a relative position of the sample cell and the objective lens, wherein at the second focusing position the objective lens focuses with respect to a second reference mark of the sample cell, wherein the second reference mark is distanced from the first reference mark;
introducing a liquid sample containing cells, into an internal space of the sample cell;
moving the sample cell and the objective lens in the first and second direction, respectively, thereby changing the relative position of the sample cell and the objective lens from the first focusing position to the second focusing position without stopping; and
taking, at a plurality of imaging positions between the first and second focusing positions, images of cells contained in the liquid sample held in the internal space, while continuously moving the sample cell and the objective lens in the first and second directions, respectively.

* * * * *